(12) United States Patent
Woodley et al.

(10) Patent No.: US 9,220,398 B2
(45) Date of Patent: Dec. 29, 2015

(54) SYSTEM FOR MANAGING BOWDEN CABLES IN ARTICULATING INSTRUMENTS

(75) Inventors: Bruce Robert Woodley, Palo Alto, CA (US); Joshua Oen, Fremont, CA (US); Aaron Brown, Vancouver, WA (US); Chris Julian, Los Gatos, CA (US); Keith P. Laby, San Francisco, CA (US); Wade Keller, Aliso Viejo, CA (US); Lawrence Kerver, Los Gatos, CA (US); Marc Kreidler, Sunnyvale, CA (US); Scott Reiner, Truckee, CA (US); Katherine Whitin, Redwood City, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1762 days.

(21) Appl. No.: 11/871,104

(22) Filed: Oct. 11, 2007

(65) Prior Publication Data

US 2009/0099420 A1    Apr. 16, 2009

(51) Int. Cl.
*A61B 1/005* (2006.01)
*B25J 9/06* (2006.01)
*G02B 23/24* (2006.01)

(52) U.S. Cl.
CPC .............. *A61B 1/0055* (2013.01); *A61B 1/0053* (2013.01); *A61B 1/0057* (2013.01); *B25J 9/065* (2013.01); *G02B 23/2476* (2013.01)

(58) Field of Classification Search
CPC .. A61B 1/0057; A61B 1/0055; A61B 1/0053; A61B 1/005; A61B 1/018; A61B 1/01; A61B 1/31; A61B 2019/2211; G02B 23/2476; B25J 9/06; B25J 9/065; Y10S 901/21; Y10S 901/15; Y10S 901/28

USPC ...................... 74/502.4–502.6, 501.6, 500.5, 74/490.04–490.06, 490.01, 490.02; 600/139–142, 144, 146–153, 114, 104, 600/106; 604/95.01–95.05, 528, 525; 138/129, 134, 135; 901/19, 21
See application file for complete search history.

(56) References Cited

U.S. PATENT DOCUMENTS 616,672 A     12/1898  Kelling
1,133,070 A *  3/1915  Subers ........................... 138/135
(Continued)

FOREIGN PATENT DOCUMENTS

DE    2823025    12/1979
DE    3707787     9/1988
(Continued)

OTHER PUBLICATIONS

Belson et al; U.S. Appl. No. 11/796,220 entitled "Steerable segmented endoscope and method of insertion," filed Apr. 27, 2007.
(Continued)

*Primary Examiner* — Daniel Yabut

(57) ABSTRACT

The present invention relates, generally, to the reduction or elimination of permanent and catastrophic herniations in Bowden cables or coil pipes in articulating devices or snake-like robots. More particularly, the present invention relates managing the coil pipes in a spiral pattern along the articulating device or snake-like robot to reduce or eliminate the necessity of the Bowden cables or coil pipes to slide along the length of the articulating device or snake-like robot. Reduction or elimination of the necessity for the Bowden cables or coil pipes to slide reduces or eliminates catastrophic herniations in articulating devices or snake-like robots undergoing one or more articulations.

25 Claims, 19 Drawing Sheets

(56) References Cited

U.S. PATENT DOCUMENTS

| | | | |
|---|---|---|---|
| 2,087,373 A * | 7/1937 | Dodge | 464/174 |
| 2,510,198 A | 6/1950 | Tesmer | |
| 2,533,494 A | 12/1950 | Mitchell, Jr. | |
| 2,767,705 A | 10/1956 | Moore | |
| 2,874,722 A * | 2/1959 | Hamblin | 138/134 |
| 3,060,972 A | 10/1962 | Sheldon | |
| 3,071,161 A | 1/1963 | Ulrich | |
| 3,096,962 A | 7/1963 | Meijs | |
| 3,162,214 A | 12/1964 | Bazinet, Jr. | |
| 3,168,274 A | 2/1965 | Street | |
| 3,190,286 A | 6/1965 | Stokes | |
| 3,266,059 A | 8/1966 | Stelle | |
| 3,430,662 A | 3/1969 | Guarnaschelli | |
| 3,435,634 A * | 4/1969 | Chatham | 464/174 |
| 3,497,083 A * | 2/1970 | Anderson et al. | 414/738 |
| 3,546,961 A | 12/1970 | Marton | |
| 3,610,231 A | 10/1971 | Takahashi | |
| 3,625,084 A | 12/1971 | Low | |
| 3,643,653 A | 2/1972 | Takahashi et al. | |
| 3,739,770 A | 6/1973 | Mori | |
| 3,773,034 A | 11/1973 | Burns et al. | |
| 3,780,740 A | 12/1973 | Rhea | |
| 3,858,578 A | 1/1975 | Milo | |
| 3,871,358 A | 3/1975 | Fukuda et al. | |
| 3,897,775 A | 8/1975 | Furihata | |
| 3,913,565 A | 10/1975 | Kawahara | |
| 3,946,727 A | 3/1976 | Okada | |
| 3,990,434 A | 11/1976 | Free | |
| 4,054,128 A | 10/1977 | Seufert | |
| 4,176,662 A | 12/1979 | Frazer | |
| 4,233,981 A | 11/1980 | Schomacher | |
| 4,236,509 A | 12/1980 | Takahashi | |
| 4,240,435 A | 12/1980 | Yazawa et al. | |
| 4,273,111 A | 6/1981 | Tsukaya | |
| 4,327,711 A | 5/1982 | Takagi | |
| 4,366,810 A | 1/1983 | Slanetz, Jr. | |
| 4,393,728 A | 7/1983 | Larson | |
| 4,432,349 A | 2/1984 | Oshiro | |
| 4,483,326 A | 11/1984 | Yamaka et al. | |
| 4,489,826 A | 12/1984 | Dubson | |
| 4,494,417 A | 1/1985 | Larson | |
| 4,499,895 A | 2/1985 | Takayama | |
| 4,503,842 A | 3/1985 | Takayama | |
| 4,543,090 A | 9/1985 | McCoy | |
| 4,551,061 A | 11/1985 | Olenick | |
| 4,559,928 A | 12/1985 | Takayama | |
| 4,566,843 A | 1/1986 | Iwatsuka | |
| 4,577,621 A | 3/1986 | Patel | |
| 4,592,341 A | 6/1986 | Omagari et al. | |
| 4,601,283 A | 7/1986 | Chikama | |
| 4,601,713 A | 7/1986 | Fuqua | |
| 4,621,618 A | 11/1986 | Omagari | |
| 4,624,243 A | 11/1986 | Lowery et al. | |
| 4,630,649 A | 12/1986 | Oku | |
| 4,643,184 A | 2/1987 | Mobin-Uddin | |
| 4,646,722 A | 3/1987 | Silverstein et al. | |
| 4,648,733 A | 3/1987 | Merkt | |
| 4,651,718 A | 3/1987 | Collins et al. | |
| 4,655,257 A | 4/1987 | Iwashita | |
| 4,683,773 A | 8/1987 | Diamond | |
| 4,686,963 A | 8/1987 | Cohen et al. | |
| 4,712,969 A | 12/1987 | Kimura | |
| 4,726,355 A | 2/1988 | Okada | |
| 4,753,222 A | 6/1988 | Morishita | |
| 4,753,223 A | 6/1988 | Bremer | |
| 4,754,909 A | 7/1988 | Barker et al. | |
| 4,784,117 A | 11/1988 | Miyazaki | |
| 4,787,369 A | 11/1988 | Allred, III | |
| 4,788,967 A | 12/1988 | Ueda | |
| 4,793,326 A | 12/1988 | Shishido | |
| 4,796,607 A | 1/1989 | Allred, III | |
| 4,799,474 A | 1/1989 | Ueda | |
| 4,800,890 A | 1/1989 | Cramer | |
| 4,807,593 A | 2/1989 | Ito | |
| 4,815,450 A | 3/1989 | Patel | |
| 4,832,473 A | 5/1989 | Ueda | |
| 4,834,068 A | 5/1989 | Gottesman | |
| 4,873,965 A | 10/1989 | Danieli | |
| 4,873,990 A | 10/1989 | Holmes et al. | |
| 4,879,991 A | 11/1989 | Ogiu | |
| 4,884,557 A | 12/1989 | Takehana et al. | |
| 4,890,602 A | 1/1990 | Hake | |
| 4,895,431 A | 1/1990 | Tsujiuchi et al. | |
| 4,899,731 A | 2/1990 | Takayama et al. | |
| 4,904,048 A | 2/1990 | Sogawa et al. | |
| 4,917,114 A | 4/1990 | Green et al. | |
| 4,919,112 A | 4/1990 | Siegmund | |
| 4,930,494 A | 6/1990 | Takehana et al. | |
| 4,949,927 A | 8/1990 | Madocks et al. | |
| 4,957,486 A | 9/1990 | Davis | |
| 4,969,709 A | 11/1990 | Sogawa et al. | |
| 4,971,035 A | 11/1990 | Ito | |
| 4,977,886 A | 12/1990 | Takehana et al. | |
| 4,977,887 A | 12/1990 | Gouda | |
| 4,987,314 A | 1/1991 | Gotanda et al. | |
| 5,005,558 A | 4/1991 | Aomori | |
| 5,005,559 A | 4/1991 | Blanco et al. | |
| 5,014,709 A | 5/1991 | Bjelkhagen et al. | |
| 5,018,509 A | 5/1991 | Suzuki et al. | |
| 5,025,778 A | 6/1991 | Silverstein et al. | |
| 5,060,632 A | 10/1991 | Hibino et al. | |
| 5,092,901 A | 3/1992 | Hunter et al. | |
| 5,125,395 A | 6/1992 | Adair | |
| 5,127,393 A | 7/1992 | McFarlin et al. | |
| 5,159,446 A | 10/1992 | Hibino et al. | |
| 5,166,787 A | 11/1992 | Irion | |
| 5,174,276 A | 12/1992 | Crockard | |
| 5,174,277 A | 12/1992 | Matsumaru | |
| 5,188,111 A | 2/1993 | Yates et al. | |
| 5,207,695 A | 5/1993 | Trout, III | |
| 5,217,001 A | 6/1993 | Nakao et al. | |
| 5,220,911 A | 6/1993 | Tamura | |
| 5,228,429 A | 7/1993 | Hatano | |
| 5,234,448 A | 8/1993 | Wholey et al. | |
| 5,243,967 A | 9/1993 | Hibino | |
| 5,250,058 A | 10/1993 | Miller et al. | |
| 5,251,611 A | 10/1993 | Zehel et al. | |
| 5,253,647 A | 10/1993 | Takahashi | |
| 5,254,809 A | 10/1993 | Martin | |
| 5,257,617 A | 11/1993 | Takahashi | |
| 5,259,364 A | 11/1993 | Bob et al. | |
| 5,271,381 A | 12/1993 | Ailinger et al. | |
| 5,271,382 A | 12/1993 | Chikama | |
| 5,279,610 A | 1/1994 | Park et al. | |
| 5,297,443 A | 3/1994 | Wentz | |
| 5,325,845 A | 7/1994 | Adair | |
| 5,337,732 A | 8/1994 | Grundfest et al. | |
| 5,337,733 A | 8/1994 | Bauerfeind | |
| 5,343,874 A | 9/1994 | Picha | |
| 5,347,987 A | 9/1994 | Feldstein et al. | |
| 5,348,259 A | 9/1994 | Blanco et al. | |
| 5,370,108 A | 12/1994 | Miura et al. | |
| 5,383,467 A | 1/1995 | Auer et al. | |
| 5,383,852 A | 1/1995 | Stevens-Wright | |
| 5,389,222 A | 2/1995 | Shahinpoor | |
| 5,394,864 A | 3/1995 | Kobayashi et al. | |
| 5,400,769 A | 3/1995 | Tanii et al. | |
| 5,402,768 A | 4/1995 | Adair | |
| 5,411,508 A | 5/1995 | Bessler et al. | |
| 5,413,108 A | 5/1995 | Alfano | |
| 5,421,337 A | 6/1995 | Richards-Kortum et al. | |
| 5,425,738 A | 6/1995 | Gustafson et al. | |
| 5,429,118 A | 7/1995 | Cole et al. | |
| 5,439,000 A | 8/1995 | Gunderson et al. | |
| 5,451,221 A | 9/1995 | Cho et al. | |
| 5,456,714 A | 10/1995 | Owen | |
| 5,460,166 A | 10/1995 | Yabe et al. | |
| 5,460,168 A | 10/1995 | Masubuchi et al. | |
| 5,469,840 A | 11/1995 | Tanii et al. | |
| 5,482,029 A | 1/1996 | Sekiguchi et al. | |
| 5,487,757 A | 1/1996 | Truckai et al. | |
| 5,489,256 A | 2/1996 | Adair | |
| 5,507,287 A | 4/1996 | Palcic et al. | |
| 5,507,717 A | 4/1996 | Kura et al. | |

(56) References Cited

U.S. PATENT DOCUMENTS

| | | |
|---|---|---|
| 5,531,664 A | 7/1996 | Adachi et al. |
| 5,551,945 A | 9/1996 | Yabe et al. |
| 5,558,619 A | 9/1996 | Kami et al. |
| 5,558,665 A | 9/1996 | Kieturakis |
| 5,577,992 A | 11/1996 | Chiba et al. |
| 5,586,968 A | 12/1996 | Grundl et al. |
| 5,590,660 A | 1/1997 | MacAulay et al. |
| 5,601,087 A | 2/1997 | Gunderson et al. |
| 5,602,449 A | 2/1997 | Krause |
| 5,620,408 A | 4/1997 | Vennes et al. |
| 5,624,380 A | 4/1997 | Takayama et al. |
| 5,624,381 A | 4/1997 | Kieturakis |
| 5,626,553 A | 5/1997 | Frassica et al. |
| 5,645,520 A | 7/1997 | Nakamura et al. |
| 5,647,368 A | 7/1997 | Zeng et al. |
| 5,651,769 A | 7/1997 | Waxman et al. |
| 5,653,690 A | 8/1997 | Booth et al. |
| 5,658,238 A | 8/1997 | Suzuki et al. |
| 5,662,585 A | 9/1997 | Willis et al. |
| 5,662,587 A | 9/1997 | Grundfest et al. |
| 5,665,050 A | 9/1997 | Benecke |
| 5,667,476 A | 9/1997 | Frassica et al. |
| 5,679,216 A | 10/1997 | Takayama et al. |
| 5,728,044 A | 3/1998 | Shan |
| 5,733,245 A | 3/1998 | Kawano |
| 5,749,828 A | 5/1998 | Solomon et al. |
| 5,752,912 A | 5/1998 | Takahashi et al. |
| 5,759,151 A | 6/1998 | Sturges |
| 5,762,613 A | 6/1998 | Sutton et al. |
| 5,765,561 A | 6/1998 | Chen et al. |
| 5,769,792 A | 6/1998 | Palcic et al. |
| 5,772,597 A | 6/1998 | Goldberger et al. |
| 5,773,835 A | 6/1998 | Sinofsky |
| 5,779,624 A | 7/1998 | Chang |
| 5,807,241 A | 9/1998 | Heimberger |
| 5,810,715 A | 9/1998 | Moriyama |
| 5,810,716 A | 9/1998 | Mukherjee |
| 5,810,717 A | 9/1998 | Maeda |
| 5,810,776 A | 9/1998 | Bacich et al. |
| 5,813,976 A | 9/1998 | Filipi et al. |
| 5,827,190 A | 10/1998 | Palcic et al. |
| 5,842,973 A | 12/1998 | Bullard |
| 5,860,581 A | 1/1999 | Robertson et al. |
| 5,860,914 A | 1/1999 | Chiba et al. |
| 5,876,329 A | 3/1999 | Harhen |
| 5,876,373 A | 3/1999 | Giba et al. |
| 5,885,208 A | 3/1999 | Moriyama |
| 5,893,369 A | 4/1999 | LeMole |
| 5,897,417 A | 4/1999 | Grey |
| 5,897,488 A | 4/1999 | Ueda |
| 5,902,254 A | 5/1999 | Magram |
| 5,906,591 A | 5/1999 | Dario et al. |
| 5,908,381 A | 6/1999 | Aznoian et al. |
| 5,916,147 A | 6/1999 | Boury |
| 5,921,915 A | 7/1999 | Aznoian et al. |
| 5,928,136 A | 7/1999 | Barry |
| 5,941,815 A | 8/1999 | Chang |
| 5,941,908 A | 8/1999 | Goldsteen et al. |
| 5,957,833 A | 9/1999 | Shan |
| 5,968,052 A | 10/1999 | Sullivan et al. |
| 5,971,767 A | 10/1999 | Kaufman et al. |
| 5,976,074 A | 11/1999 | Moriyama |
| 5,989,182 A | 11/1999 | Hori et al. |
| 5,989,230 A | 11/1999 | Frassica |
| 5,993,381 A | 11/1999 | Ito |
| 5,993,447 A | 11/1999 | Blewett et al. |
| 5,996,346 A | 12/1999 | Maynard |
| 6,016,440 A | 1/2000 | Simon et al. |
| 6,033,359 A | 3/2000 | Doi |
| 6,036,636 A | 3/2000 | Motoki et al. |
| 6,042,155 A | 3/2000 | Lockwood |
| 6,048,307 A | 4/2000 | Grundl et al. |
| 6,063,022 A | 5/2000 | Ben-Haim |
| 6,066,102 A | 5/2000 | Townsend et al. |
| 6,066,132 A | 5/2000 | Chen et al. |
| 6,068,638 A | 5/2000 | Makower |
| 6,096,289 A | 8/2000 | Goldenberg |
| 6,099,464 A | 8/2000 | Shimizu et al. |
| 6,099,465 A | 8/2000 | Inoue |
| 6,099,485 A | 8/2000 | Patterson |
| 6,106,510 A | 8/2000 | Lunn et al. |
| 6,119,913 A | 9/2000 | Adams et al. |
| 6,129,667 A | 10/2000 | Dumoulin et al. |
| 6,129,683 A | 10/2000 | Sutton et al. |
| 6,141,577 A | 10/2000 | Roland |
| 6,149,581 A | 11/2000 | Klingenstein |
| 6,162,171 A | 12/2000 | Ng et al. |
| 6,174,280 B1 | 1/2001 | Oneda |
| 6,174,291 B1 | 1/2001 | McMahon et al. |
| 6,179,776 B1 | 1/2001 | Adams |
| 6,185,448 B1 | 2/2001 | Borovsky |
| 6,201,989 B1 | 3/2001 | Whitehead |
| 6,203,493 B1 | 3/2001 | Ben-Haim |
| 6,203,494 B1 | 3/2001 | Moriyama |
| 6,210,337 B1 | 4/2001 | Dunham et al. |
| 6,221,006 B1 | 4/2001 | Dubrul et al. |
| 6,241,657 B1 | 6/2001 | Chen et al. |
| 6,249,076 B1 | 6/2001 | Madden et al. |
| 6,270,453 B1 | 8/2001 | Sakai |
| 6,306,081 B1 | 10/2001 | Ishikawa et al. |
| 6,309,346 B1 | 10/2001 | Farhadi |
| 6,315,714 B1 | 11/2001 | Akiba |
| 6,319,197 B1 | 11/2001 | Tsuji et al. |
| 6,327,492 B1 | 12/2001 | Lemelson |
| 6,332,089 B1 | 12/2001 | Acker |
| 6,348,058 B1 | 2/2002 | Melkent |
| 6,366,799 B1 | 4/2002 | Acker |
| 6,402,687 B1 | 6/2002 | Ouchi |
| 6,408,889 B1 | 6/2002 | Komachi |
| 6,428,203 B1 | 8/2002 | Danley |
| 6,443,888 B1 | 9/2002 | Ogura et al. |
| 6,453,190 B1 | 9/2002 | Acker |
| 6,459,481 B1 | 10/2002 | Schaack |
| 6,468,203 B2 | 10/2002 | Belson |
| 6,482,149 B1 | 11/2002 | Torii |
| 6,485,413 B1 | 11/2002 | Boppart |
| 6,490,467 B1 | 12/2002 | Bucholz |
| 6,511,417 B1 | 1/2003 | Taniguchi |
| 6,511,418 B2 | 1/2003 | Shahidi |
| 6,517,477 B1 | 2/2003 | Wendlandt |
| 6,527,706 B2 | 3/2003 | Ide |
| 6,537,211 B1 | 3/2003 | Wang et al. |
| 6,544,215 B1 | 4/2003 | Bencini et al. |
| 6,554,793 B1 | 4/2003 | Pauker et al. |
| 6,569,173 B1 | 5/2003 | Blatter et al. |
| 6,616,600 B2 | 9/2003 | Pauker |
| 6,638,213 B2 | 10/2003 | Ogura et al. |
| 6,641,528 B2 | 11/2003 | Torii |
| 6,656,110 B1 | 12/2003 | Irion et al. |
| 6,699,183 B1 | 3/2004 | Wimmer |
| 6,761,685 B2 | 7/2004 | Adams et al. |
| 6,783,491 B2 | 8/2004 | Saadat et al. |
| 6,790,173 B2 | 9/2004 | Saadat et al. |
| 6,800,056 B2 | 10/2004 | Tartaglia et al. |
| 6,808,499 B1 | 10/2004 | Churchill et al. |
| 6,808,520 B1 | 10/2004 | Fourkas et al. |
| 6,817,973 B2 | 11/2004 | Merril et al. |
| 6,827,108 B2 * | 12/2004 | Bakker .................. 138/118 |
| 6,837,846 B2 | 1/2005 | Jaffe |
| 6,837,847 B2 | 1/2005 | Ewers et al. |
| 6,837,849 B2 | 1/2005 | Ogura et al. |
| 6,843,793 B2 | 1/2005 | Brock et al. |
| 6,850,794 B2 | 2/2005 | Shahidi |
| 6,858,005 B2 * | 2/2005 | Ohline et al. .................. 600/141 |
| 6,869,396 B2 | 3/2005 | Belson |
| 6,875,170 B2 | 4/2005 | Francois et al. |
| 6,887,195 B1 * | 5/2005 | Pilvisto .................. 600/141 |
| 6,890,297 B2 | 5/2005 | Belson |
| 6,902,528 B1 | 6/2005 | Garibaldi et al. |
| 6,942,613 B2 | 9/2005 | Ewers et al. |
| 6,960,161 B2 | 11/2005 | Amling et al. |
| 6,960,162 B2 | 11/2005 | Saadat et al. |
| 6,960,163 B2 | 11/2005 | Ewers et al. |
| 6,974,411 B2 | 12/2005 | Belson |

(56) References Cited

U.S. PATENT DOCUMENTS

| | | |
|---|---|---|
| 6,984,203 B2 | 1/2006 | Tartaglia et al. |
| 7,018,331 B2 | 3/2006 | Chang et al. |
| 7,087,013 B2 | 8/2006 | Belson et al. |
| 8,182,418 B2 * | 5/2012 | Durant et al. ............... 600/142 |
| 8,608,647 B2 * | 12/2013 | Durant et al. ............... 600/141 |
| 2001/0053874 A1 * | 12/2001 | Pauker ............................ 600/152 |
| 2002/0016607 A1 | 2/2002 | Bonadio et al. |
| 2002/0062062 A1 | 5/2002 | Belson et al. |
| 2002/0120254 A1 | 8/2002 | Julian |
| 2002/0147385 A1 | 10/2002 | Butler et al. |
| 2002/0151767 A1 | 10/2002 | Sonnenschein |
| 2002/0169361 A1 | 11/2002 | Taniguchi |
| 2002/0193662 A1 | 12/2002 | Belson |
| 2003/0083550 A1 | 5/2003 | Miyagi |
| 2003/0130598 A1 | 7/2003 | Manning et al. |
| 2003/0167007 A1 | 9/2003 | Belson |
| 2003/0182091 A1 | 9/2003 | Kukuk |
| 2003/0195387 A1 | 10/2003 | Kortenbach et al. |
| 2003/0233056 A1 | 12/2003 | Saadat et al. |
| 2003/0236505 A1 | 12/2003 | Bonadio et al. |
| 2003/0236549 A1 | 12/2003 | Bonadio et al. |
| 2004/0019254 A1 | 1/2004 | Belson |
| 2004/0044270 A1 | 3/2004 | Barry |
| 2004/0049251 A1 | 3/2004 | Knowlton |
| 2004/0097788 A1 | 5/2004 | Mourlas et al. |
| 2004/0106852 A1 | 6/2004 | Windheuser et al. |
| 2004/0176683 A1 | 9/2004 | Whitin et al. |
| 2004/0186350 A1 | 9/2004 | Brenneman et al. |
| 2004/0193008 A1 | 9/2004 | Jaffe et al. |
| 2004/0193009 A1 | 9/2004 | Jaffe et al. |
| 2004/0210109 A1 | 10/2004 | Jaffe et al. |
| 2004/0220450 A1 | 11/2004 | Jaffe et al. |
| 2004/0230096 A1 | 11/2004 | Stefanchik et al. |
| 2005/0020901 A1 | 1/2005 | Belson et al. |
| 2005/0085693 A1 | 4/2005 | Belson et al. |
| 2005/0124855 A1 | 6/2005 | Jaffe et al. |
| 2005/0137454 A1 | 6/2005 | Saadat et al. |
| 2005/0137455 A1 | 6/2005 | Ewers et al. |
| 2005/0137456 A1 | 6/2005 | Saadat et al. |
| 2005/0154258 A1 | 7/2005 | Tartaglia et al. |
| 2005/0154261 A1 * | 7/2005 | Ohline et al. ............... 600/141 |
| 2005/0165276 A1 | 7/2005 | Belson |
| 2005/0168571 A1 | 8/2005 | Lia et al. |
| 2005/0203339 A1 | 9/2005 | Butler et al. |
| 2005/0209506 A1 | 9/2005 | Butler et al. |
| 2005/0209509 A1 | 9/2005 | Belson |
| 2005/0222497 A1 | 10/2005 | Belson |
| 2005/0222498 A1 | 10/2005 | Belson |
| 2005/0250990 A1 | 11/2005 | Le et al. |
| 2006/0009678 A1 | 1/2006 | Jaffe et al. |
| 2006/0052664 A1 | 3/2006 | Julian et al. |
| 2006/0146127 A1 * | 7/2006 | Bagley et al. ................... 348/83 |
| 2006/0199999 A1 * | 9/2006 | Ikeda et al. ................... 600/141 |
| 2006/0235457 A1 | 10/2006 | Belson |
| 2006/0235458 A1 | 10/2006 | Belson |
| 2006/0258912 A1 | 11/2006 | Belson et al. |
| 2007/0043259 A1 | 2/2007 | Jaffe et al. |
| 2007/0093858 A1 | 4/2007 | Gambale et al. |
| 2007/0135803 A1 | 6/2007 | Belson |
| 2007/0161291 A1 | 7/2007 | Swinehart et al. |
| 2007/0161857 A1 | 7/2007 | Durant et al. |
| 2007/0249901 A1 | 10/2007 | Ohline et al. |
| 2007/0270650 A1 | 11/2007 | Eno et al. |
| 2008/0154288 A1 | 6/2008 | Belson |
| 2008/0262538 A1 * | 10/2008 | Danitz et al. ............... 606/205 |
| 2009/0044654 A1 * | 2/2009 | Vaccani ..................... 74/490.01 |
| 2012/0265215 A1 * | 10/2012 | Durant et al. ............... 606/130 |

FOREIGN PATENT DOCUMENTS

| | | |
|---|---|---|
| DE | 4102211 A1 | 8/1991 |
| DE | 19626433 A1 | 1/1998 |
| DE | 19729499 A1 | 1/1999 |
| EP | 165718 A2 * | 12/1985 |
| EP | 0165718 A2 | 12/1985 |
| EP | 0382974 A1 | 8/1990 |
| EP | 0497781 B1 | 1/1994 |
| EP | 0993804 A1 | 4/2000 |
| EP | 1101442 A2 | 5/2001 |
| EP | 1681013 A1 | 7/2006 |
| FR | 2732225 A1 | 10/1996 |
| GB | 2347685 A | 9/2000 |
| IE | 2000/0225 | 3/2000 |
| IE | 2000/0559 | 7/2000 |
| IE | 2002/0170 | 3/2002 |
| JP | 63136014 | 6/1988 |
| JP | 63272322 | 11/1988 |
| JP | 1152413 | 6/1989 |
| JP | 1229220 | 9/1989 |
| JP | 01-262372 | 10/1989 |
| JP | 2246986 | 10/1990 |
| JP | 2296209 | 12/1990 |
| JP | 3136630 | 6/1991 |
| JP | 4054970 | 2/1992 |
| JP | 5011196 | 1/1993 |
| JP | 5111458 | 5/1993 |
| JP | 5305073 | 11/1993 |
| JP | 06-007287 | 1/1994 |
| JP | 08-322786 | 12/1996 |
| JP | 09-028662 | 2/1997 |
| JP | 10337274 | 12/1998 |
| JP | 11042258 | 2/1999 |
| JP | 2001-046318 | 2/2001 |
| SU | 871786 | 10/1981 |
| SU | 1256955 | 9/1986 |
| SU | 1301701 | 4/1987 |
| WO | WO 93/17751 A1 | 9/1993 |
| WO | WO 94/19051 A1 | 9/1994 |
| WO | WO 95/04556 A2 | 2/1995 |
| WO | WO 95/09562 A1 | 4/1995 |
| WO | WO 96/05768 A1 | 2/1996 |
| WO | WO 97/10746 A1 | 3/1997 |
| WO | WO 97/25101 A2 | 7/1997 |
| WO | WO 97/29701 A1 | 8/1997 |
| WO | WO 97/29710 A1 | 8/1997 |
| WO | WO 98/24017 A2 | 6/1998 |
| WO | WO 98/49938 A1 | 11/1998 |
| WO | WO 99/16359 A1 | 4/1999 |
| WO | WO99/33392 A1 | 7/1999 |
| WO | WO 99/51283 A2 | 10/1999 |
| WO | WO 99/59664 A1 | 11/1999 |
| WO | WO 00/10456 A1 | 3/2000 |
| WO | WO 00/27462 A1 | 5/2000 |
| WO | WO 00/54653 A1 | 9/2000 |
| WO | WO 00/74565 A1 | 12/2000 |
| WO | WO 01/49353 A2 | 7/2001 |
| WO | WO 01/67964 A2 | 9/2001 |
| WO | WO 01/70096 A1 | 9/2001 |
| WO | WO 01/70097 A1 | 9/2001 |
| WO | WO 01/74235 A1 | 10/2001 |
| WO | WO 01/80935 A1 | 11/2001 |
| WO | WO 02/24058 A2 | 3/2002 |
| WO | WO 02/39909 A1 | 5/2002 |
| WO | WO 02/47549 A1 | 6/2002 |
| WO | WO 02/064028 A1 | 8/2002 |
| WO | WO 02/068988 A1 | 9/2002 |
| WO | WO 02/069841 A2 | 9/2002 |
| WO | WO 02/089692 A1 | 11/2002 |
| WO | WO 02/096276 A1 | 12/2002 |
| WO | WO 03/028547 A2 | 4/2003 |
| WO | WO 03/073920 A2 | 9/2003 |
| WO | WO 03/073921 A1 | 9/2003 |
| WO | WO 03/092476 A2 | 11/2003 |
| WO | WO 2004/006980 A2 | 1/2004 |
| WO | WO 2004/019769 A1 | 3/2004 |
| WO | WO 2004/049905 A2 | 6/2004 |

(56) References Cited

FOREIGN PATENT DOCUMENTS

| WO | WO 2004/071284 A1 | 8/2004 |
|----|-------------------|--------|
| WO | WO 2004/080313 A1 | 9/2004 |
| WO | WO 2004/084702 A1 | 10/2004 |
| WO | WO 2005/084542 A1 | 9/2005 |
| WO | WO2006/134881 | 12/2006 |

OTHER PUBLICATIONS

Berger, W. L. et al. Sigmoid Stiffener for Decompression Tube Placement in Colonic Pseudo-Obstruction. Endoscopy. 2000; 32 (1): 54-57.

Hasson, H.M. Technique of open laralscopy:equipment and technique. (from step 1 to step 9). May 1979, 2424 North Clark Street, Chicago, IL 60614. 3 pages.

Lee, et al. A highly redundant robot system for inspection. Proceedings of Conference on Intelligent Robotics in Field, Factory, Service, and Space (CIRFFSS "94). Mar. 21-24, 1994. 1:142-148. Houston, Texas.

McKernan, et al. Laparoscopic general surgery. Journal of the Medical Association of Georgia. 1990; 79 (3):157-159.

Science & Technology, Laptop Magazine. Oct. 2002. p. 98.

Slatkin, et al. The development of a robotic endoscope. Proceedings 1995 IEEE/RSJ International Conference on Intelligent Robots and Systems. Aug. 5-9, 1995. 2:162-171. Pittsburgh, Pennsylvania.

Durant, et al.; U.S. Appl. No. 12/036,976 entitled "Systems and methods for articulating an elongate body," filed Feb. 25, 2008.

PCT/US08/78662 International Search Report and Written Opinion, mailed Apr. 24, 2009, 17 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

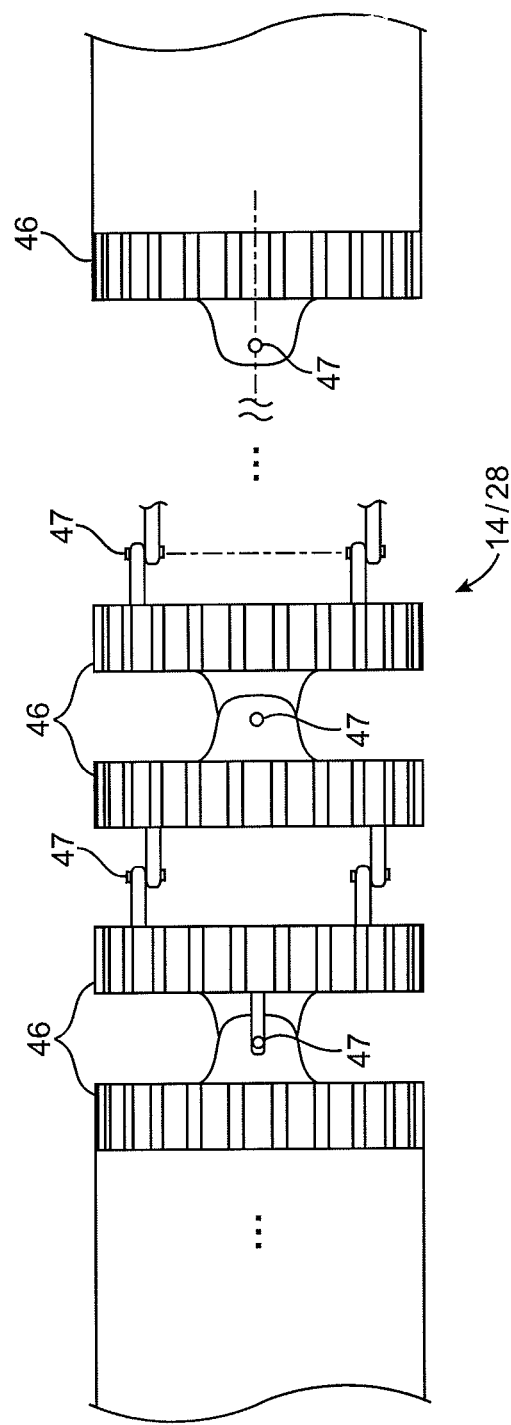

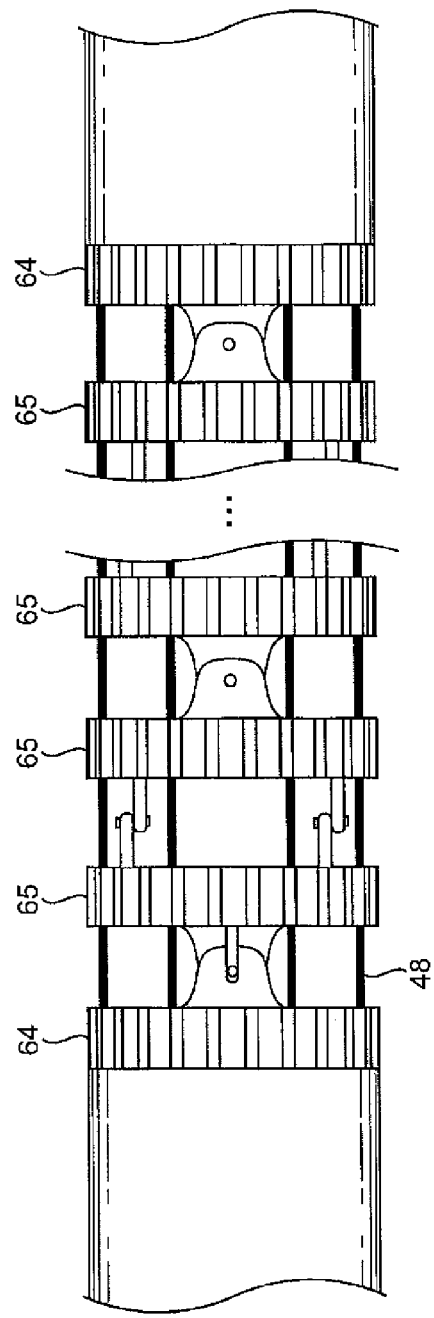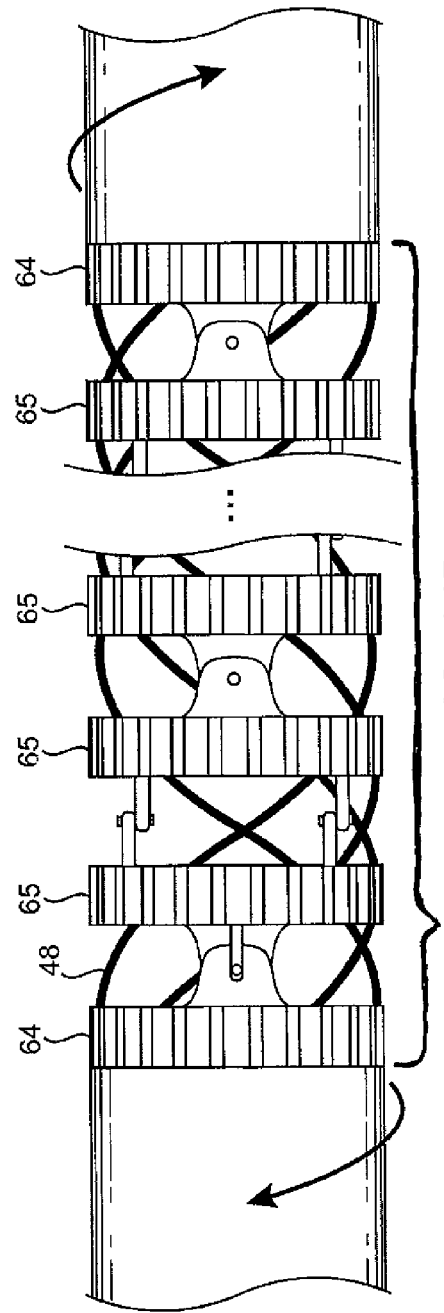

SYSTEM FOR MANAGING BOWDEN CABLES IN ARTICULATING INSTRUMENTS

All publications and patent applications mentioned in this specification are incorporated herein, in their entirety, by reference to the same extent as if each individual publication or patent application was specifically and individually indicated to be incorporated by reference.

FIELD OF THE INVENTION

The present invention relates, generally, to management of Bowden-type cables in articulating instruments or snake-like robots. More particularly, the present invention relates to managing Bowden-type cables to reduce or eliminate catastrophic permanent lateral plastic deformation (also referred to herein as kinking or herniation) of these cables in articulating instruments or snake-like robots.

BACKGROUND OF THE INVENTION

The forms of robots vary widely, but all robots share the features of a mechanical, movable structure under some form of control. The mechanical structure or kinematic chain (analogous to the human skeleton) of a robot is formed from several links (analogous to human bones), actuators (analogous to human muscle) and joints permitting one or more degrees of freedom of motion of the links. A continuum or multi-segment robot is a continuously curving device, like an elephant trunk for example. An example of a continuum or multi-segment robot is a snake-like endoscopic device, like that under investigation by NeoGuide Systems, Inc., and described in U.S. Pat. Nos. 6,468,203; 6,610,007; 6,800,056; 6,974,411; 6,984,203; 6,837,846; and 6,858,005. Another example of a snake-like robotic device is shown and described in U.S. Patent Publication US2005/0059960 to Simaan, et al.

Snake-like robots often use Bowden cables to transfer forces from an actuator to particular sections or segments of the snake-like robot to effect articulation of that section or segment. Multiple, simultaneous articulations of the snake-like robot require the Bowden cables to go through multiple tortuous paths. One challenge faced by the practitioner is that Bowden cables can herniate under overloading conditions and axial loads placed upon them as a result of articulation. Various embodiments of the present invention address this issue.

SUMMARY OF THE INVENTION

An embodiment of the present invention is a system for managing the transmission of force to articulate an elongate device or snake-like robot. The system, of this embodiment, has an elongate body comprising a plurality of articulatable segments. The system includes a plurality of coil pipes, where each coil pipe is fixed at its proximal end relative to an actuator, at its distal end relative to a proximal portion of one of the plurality of articulatable segments, and where the coil pipes extend along each segment in a spiral pattern. A plurality of tensioning members is provided, where the tensioning members are housed in the plurality of coil pipes. The proximal end of each tensioning member is coupled to the actuator, and the distal end extends out the distal end of the coil pipe and is coupled to the articulatable segment to which the distal end of the coil pipe is fixed. The coil pipe/tensioning member combination works like a Bowden cable. The tensioning of one or more of the tensioning members causes articulation of the articulatable segment. In an alternative embodiment of the present invention, the articulatable segments are constructed from at least two links and preferably at least four links jointed together. Preferably, the links are control rings, such as and without limitation vertebrae, and the joints are hinges between the vertebrae. In an alternative embodiment the spiral pattern comprises an approximate integral number of approximately full turns along each of the plurality of articulatable segments, and preferably approximately one full turn.

In an alternative system for managing the transmission of force in an articulating device, the system comprises an elongate body have a plurality of articulatable segments. Bowden cables are coupled at a proximal end to an actuator and at a distal end to a proximal portion of one of the articulatable segments. Actuation of one or more of the Bowden cables causes the articulation of one or more of the segments to which the Bowden cables are coupled. The Bowden cables extend along each segment in a spiral pattern.

In another embodiment coil pipes are constructed from approximately round wire, D-shaped wire or are centerless ground. A D-shaped coil pipe that is less susceptible to herniation or axial overloading, in accordance with an embodiment of the present invention, can comprise D-shaped wire coiled, around a mandrel, for example, into a pipe shape. The wire used to make this embodiment of coil pipe has a cross-section having two approximately parallel approximately flat sides, a convex side and a concave side approximately parallel to said convex side. Preferably, the concave side of the wire of a first coil approximately nests with the convex side of the wire in a second adjacent coil, and the approximately parallel flat sides form an interior and an exterior of the coil pipe. The convex and concave sides can have an approximately curved shape, such as and without limitation a portion of a circle. Alternatively, the convex and concave sides can have an angular shape, such as and without limitation a V-shape. Alternatively, the wire can have a square or rectangular cross-section. A coil pipe can also comprise approximately circular cross-section wire coiled, around a mandrel for example, into a pipe shape. In a further embodiment of the present invention the pipe shape is ground or otherwise has material removed to form approximately parallel exterior flat sides, thereby forming a centerless ground coil pipe.

BRIEF DESCRIPTION OF THE DRAWINGS

The novel features of the invention are set forth with particularity in the claims that follow. A better understanding of the features and advantages of the present invention will be obtained by reference to the detailed description below that sets forth illustrative embodiments, in which the principles of the invention are utilized, and the accompanying drawings.

In the drawings:

FIG. 2 depicts an embodiment of a steerable distal portion or a controllable segment of an endoscope in accordance with the present invention;

FIG. 14 provides a schematic for describing one alternative for spiraling of coil pipes along a segment in accordance with an embodiment of the present invention.

DETAILED DESCRIPTION OF THE INVENTION

Figure 1:
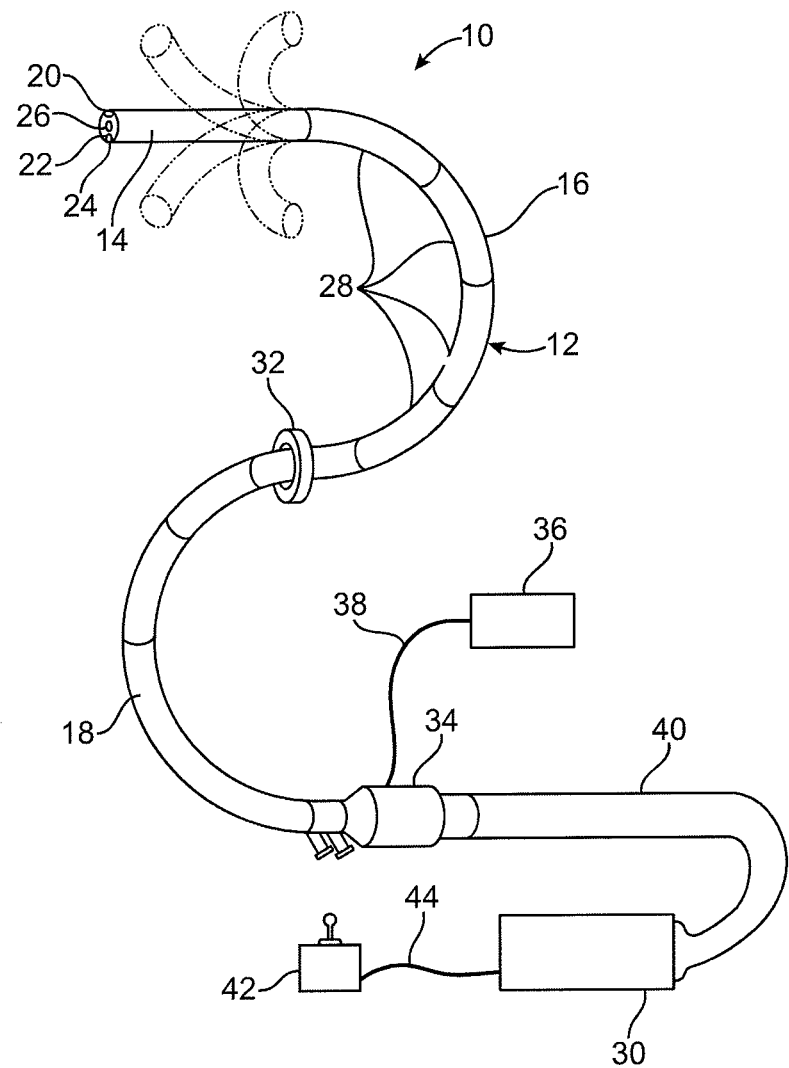
FIG. 1 depicts an endoscope in accordance with an embodiment of the present invention.

FIG. 1 depicts endoscope 10, a colonoscope in particular, in accordance with an embodiment of the present invention. Endoscope 10 has elongate body 12 with steerable distal portion 14, automatically controlled proximal portion 16, and flexible and passively manipulated proximal portion 18. The skilled artisan will appreciate that automatically controlled proximal portion 16 may also be flexible and passively manipulated, although it is preferred to provide automatically controlled proximal portion 16. The skilled artisan will also appreciate that elongate body 12 can have only steerable distal portion 14 and automatically controlled portion 16. Fiber optic imaging bundle 20 and illumination fiber(s) 22 may extend through elongate body 12 to steerable distal portion 14, or video camera 24 (e.g., CCD or CMOS camera) may be positioned at the distal end of steerable distal portion 14, as known by the skilled artisan. As the skilled artisan appreciates, a user views live or delayed video feed from video camera 24 via a video cable (e.g., wire or optical fiber, not shown) or through wireless transmission of the video signal. Typically, as will be appreciated by the skilled artisan, endoscope 10 will also include one or more access lumens, working channels, light channels, air and water channels, vacuum channels, and a host of other well known complements useful for both medical and industrial endoscopy. These channels and other amenities are shown generically as 26, because such channels and amenities are well known and appreciated by the skilled artisan.

Preferably, automatically controlled proximal portion 16 comprises a plurality of segments 28, which are controlled via computer and/or electronic controller 30. Such an automatically controlled endoscope is described in further detail in commonly assigned U.S. patent application Ser. No. 10/229,577 (now U.S. Pat. No. 6,858,005) and Ser. No. 11/750,988, both previously incorporated herein by reference. Preferably, the distal end of a tendon (more thoroughly described below) is mechanically connected to a each segment 28 or steerable distal portion 14, with the proximal end of the tendon mechanically connected to actuators to articulate segments 28 or steerable distal portion 14, which is more fully described below and in U.S. patent application Ser. No. 10/229,577 (now U.S. Pat. No. 6,858,005) and Ser. No. 11/750,988, both previously incorporated herein by reference. The actuators driving the tendons may include a variety of different types of mechanisms capable of applying a force to a tendon, e.g., electromechanical motors, pneumatic and hydraulic cylinders, pneumatic and hydraulic motors, solenoids, shape memory alloy wires, electronic rotary actuators or other devices or methods as known in the art. If shape memory alloy wires are used, they are preferably configured into several wire bundles attached at a proximal end of each of the tendons within the controller. Segment articulation may be accomplished by applying energy, e.g., electrical current, electrical voltage, heat, etc., to each of the bundles to actuate a linear motion in the wire bundles which in turn actuate the tendon movement. The linear translation of the actuators within the controller may be configured to move over a relatively short distance to accomplish effective articulation depending upon the desired degree of segment movement and articulation. In addition, the skilled artisan will also appreciate that knobs attached to rack and pinion gearing can be used to actuate the tendons attached to steerable distal portion 14. An axial motion transducer 32 (also called a depth referencing device or datum) may be provided for measuring the axial motion, i.e., the depth change, of elongate body 12 as it is advanced and withdrawn. As elongate body 12 of endoscope 10 slides through axial motion transducer 32, it indicates the axial position of the elongate body 12 with respect to a fixed point of reference. Axial motion transducer 32 is more fully described in U.S. patent application Ser. No. 10/229,577, previously incorporated herein by reference.

In the embodiment depicted in FIG. 1, handle 34 is connected to illumination source 36 by illumination cable 38 that is connected to or continuous with illumination fibers 22. Handle 34 is connected to electronic controller 30 by way of controller cable 40. Steering controller 42 (e.g., a joy stick) is connected to electronic controller 30 by way of second cable 44 or directly to handle 34. Electronic controller 30 controls the movement of the segmented automatically controlled proximal portion 16, which is described more thoroughly below and in U.S. patent application Ser. No. 11/750,988, previously incorporated herein by reference.

Referring to FIG. 2, steerable distal portion 14 and segments 28 of automatically controlled proximal portion 16 are preferably constructed from a plurality of links 46. Five links 46 are shown in this example for the sake of clarity, although the skilled artisan will recognize that any number of links may be used, the ultimate number being primarily defined by the purpose for which segments 28 or steerable distal portion 14 will be used. Each link 46 connects one joint (e.g., 47) to an adjacent joint (e.g., 47). Each link 46, in this embodiment, can move with two degrees of freedom relative to an adjacent link.

Figure 3A:
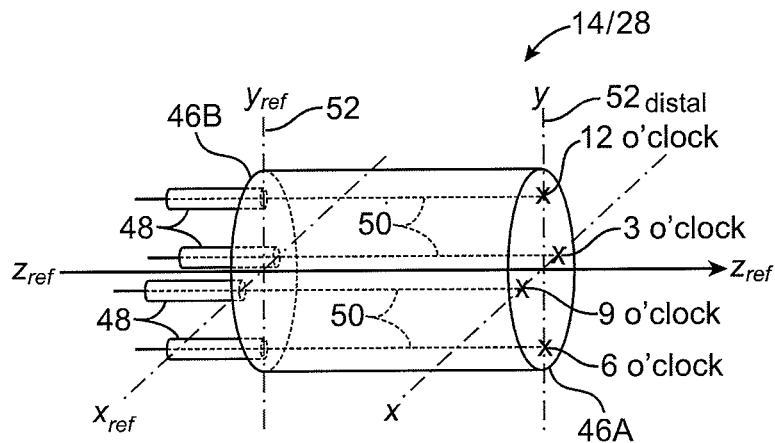
FIG. 3 depicts a schematic diagram of either a steerable distal portion or a controllable segment of an endoscope in accordance with the present invention.
Figure 3B:
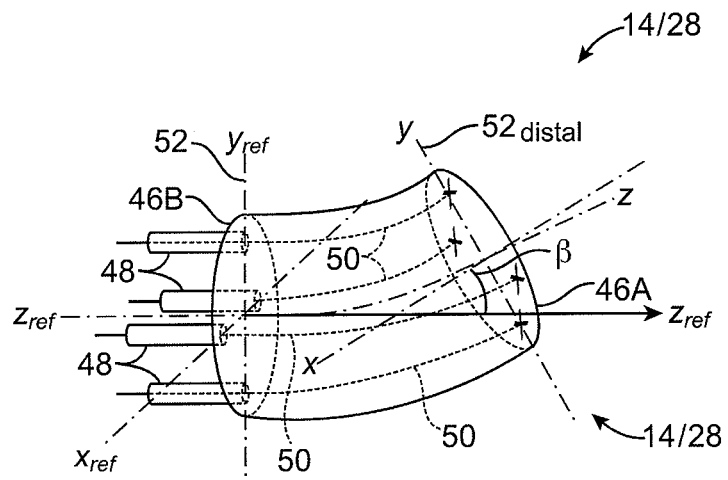
Figure 3C:
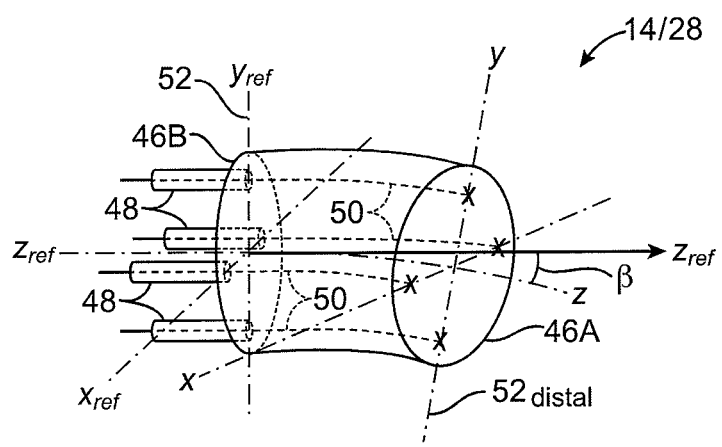

Referring now to FIG. 3A-C a schematic diagram of either steerable distal portion 14 or segments 28 is provided for discussion purposes and to explain a preferred system and method for articulating steerable distal portion 14 or segments 28. The skilled artisan will recognize that the system and method for articulation is the same for both steerable distal portion 14 and segments 28 of automatically controlled proximal portion 16. Therefore, the system and method for articulation will be described referring only to segments 28, with the recognition that the description also applies equally to steerable distal portion 14. It is noted that details relating to links 46, joints 47 and the interconnections of the links have been eliminated from this figure for the sake of clarity.

FIG. 3A shows a three-dimensional view of segment 28 in its substantially straight configuration. The most distal link 46A and most proximal link 46B are depicted as circles. Bowden cables extend down the length of elongate body 12 (not shown in FIGS. 3A-C) and comprise coil pipes 48 and tendons 50. The proximal end of the Bowden-type cable is coupled to an actuator (not shown) and the distal end is coupled to the segment for which it controls articulation. Coil pipes 48 house tendons 50 (i.e. a Bowden-type cable) along the length of elongate body 12 (not shown in FIGS. 3A-C) and coil pipes 48 are fixed at the proximal end of segment 28. Tendons 50 extend out of coil pipes 48 at the proximal end of segment 28 along the length of segment 28, and are mechanically attached to the distal portion of segment 28. It will be appreciated that the distal end of tendons 50 need only be attached to the segment being articulated by that tendon 50 at a location required to transfer the actuated force to that segment to effect articulation; the distal portion of the segment is provided by way of explanation and example, and not by way of limitation. In the variation depicted in FIG. 3A-C four tendons 50 are depicted to articulate segment 28, but more or fewer may be used. The coil pipe/tendon combination, or Bowden cables, can be used to apply force to articulate segments 28 and can be actuated remotely to deliver forces as desired to articulate segments 28. In this manner, actuation of one or more tendons 50 causes segment 28 to articulate. In the embodiment depicted, links 46 have joints 47 alternating by 90 degrees (see FIGS. 2 and 4). Thus, an assembly of multiple links 46 is able to move in many directions, limited only by the number of actuated joints. As will be appreciated by the skilled artisan, tendons 50 can be made from a variety of materials, which is primarily dictated by the purpose for which the endoscope will be used. Without limitation tendons 50 can be made from stainless steel, titanium, nitinol, ultra high molecular weight polyethylene, the latter of which is preferred, or any other suitable material known to the skilled artisan.

In the variation depicted in FIG. 3A-C, four tendons 50 are used to articulate segment 28, although more or fewer tendons could be used, as will be appreciated by the skilled artisan. Four tendons can reliably articulate segment 28 in many directions. Tendons 50 are attached at the most distal link 46A, for the purposes of this discussion but not by way of limitation, close to the edge spaced equally apart at 12, 3, 6, and 9 O'clock.

FIG. 3B-C show segment 28 articulated by independently pulling or slacking each of the four tendons 50. For example, referring to FIG. 3B, pulling on tendon 50 at the 12 O'clock position and easing tension on tendon 50 at the 6 O'clock position causes steerable distal portion 28 to articulate in the positive y-direction with respect to the z-y-x reference frame 52. It is noted that the most distal z-y-x coordinate frame $52_{distal}$ rotates with respect to the z-y-x reference frame 52 and that β is the degree of overall articulation of segment 28. In this situation β is only along the positive y-axis, up, because only tendon 50 at the 12 O'clock position was pulled while easing tension or giving slack to tendon 50 at 6 O'clock. The tendons 50 at 3- and 9 O'clock were left substantially static in this example, and, thus, had approximately no or little affect on articulation of segment 28. The reverse situation (not depicted), pulling on tendon 50 at the 6 O'clock position and slacking or easing the tension on tendon 50 at the 12 O'clock position results in articulation of segment 28 in the negative y-direction, or down. Referring to FIG. 3C the same logic applies to articulate segment 28 in the positive x-direction (right) or a negative x-direction (left, not shown). Segment 28 can be articulated in any direction by applying varying tensions to the tendons 50 off axis, e.g., applying tension to the tendons at 12 O'clock and 3 O'clock results in an articulation up and to the left.

Referring now to FIG. 4, links 46 may be control rings to provide the structure needed to construct steerable distal portion 14 and segments 28. FIG. 4A shows a first variation of a vertebra-type control ring 54 that forms segments 28 or steerable distal portion 14. FIG. 4B shows an end view of a single vertebra-type control ring 54 of this first variation. In this embodiment each vertebra-type control ring 54 define a central aperture 56 that collectively form an internal lumen of the device, which internal lumen is used to house the various access lumens, working channels, light channels, air and water channels, vacuum channels, and a host of other well known complements useful for both medical and industrial endoscopy. Vertebrae-type control rings 54 have two pairs of joints or hinges 58A and 58B; the first pair 58A projecting perpendicularly from a first face of the vertebra and a second pair 58B, located 90 degrees around the circumference from the first pair, projecting perpendicularly away from the face of the vertebra on a second face of the vertebra opposite to the first face. Hinges 58A and 58B are tab-shaped, however other shapes may also be used.

Figure 4A:
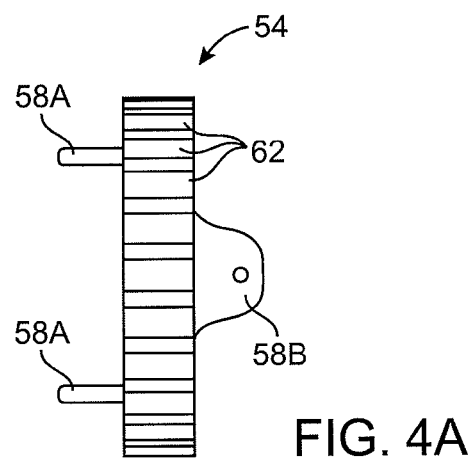
FIG. 4 depicts embodiments of vertebrae-type control rings in accordance with an embodiment of the present invention.
Figure 5:
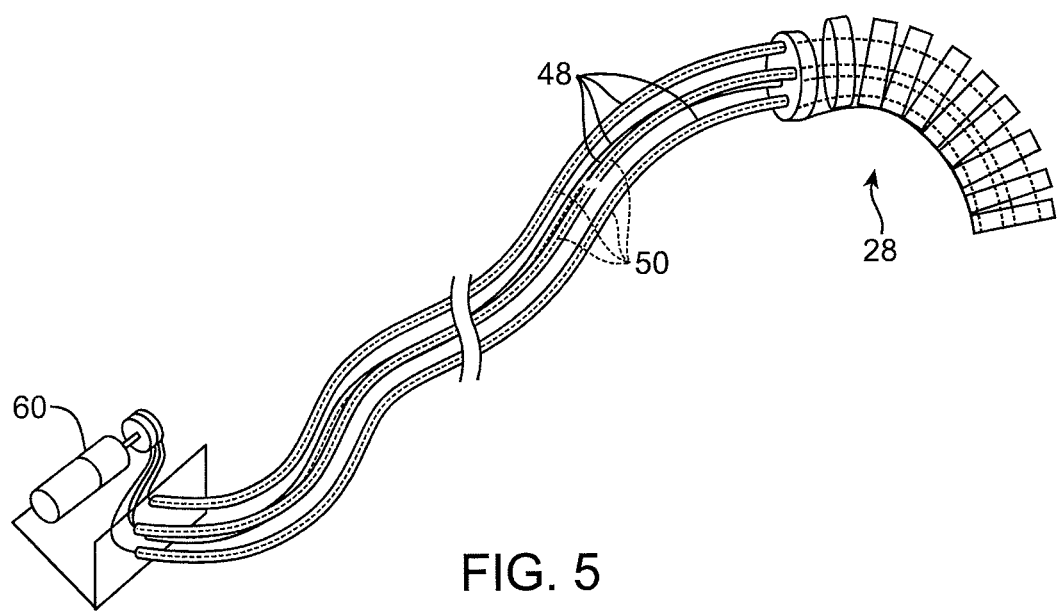
FIG. 5 depicts a schematic of how to arrange coil pipes and tendons relative to actuators and an articulatable segment or tip.

Referring briefly to FIG. 5, tension applied to tendon 50 by actuator 60 is isolated to a particular segment 28 by use of coil pipe 48 housing tendon 50, as previously described. Referring back again to FIG. 4A, vertebra-type control ring 54 is shown with four holes 60 through the edge of vertebra-type control ring 54 that may act as, e.g., attachment sites for tendon 50, as a throughway for tendon 50 in other vertebrae-type control rings 54 (links) of that particular segment 28 and/or attachment sites for coil pipes 48 when vertebra-type control ring 54 is the most proximal link in segment 28. The skilled artisan will appreciate that the number of tendons 50 used to articulate each segment 28 or tip 14 determines the number of holes 60 provided for passage of tendons 50.

Figure 4B:
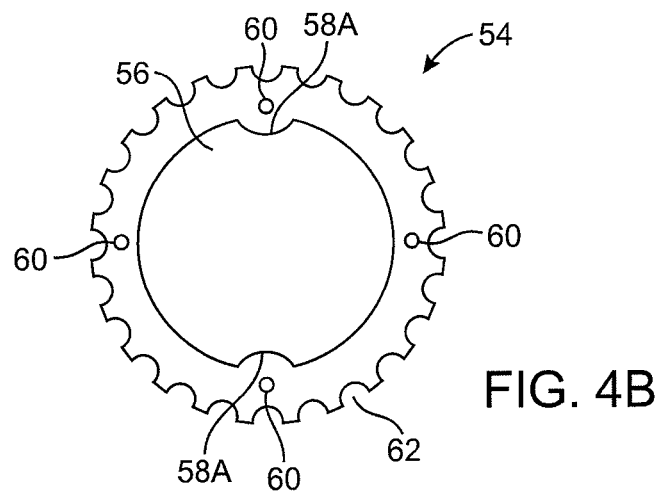
Figure 4C:
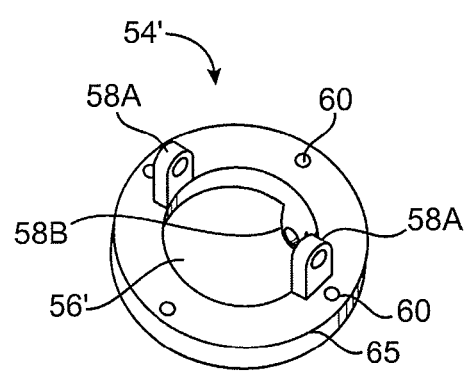

The outer edge of vertebra-type control ring 54 in the variation depicted in FIG. 4A-B may be scalloped to provide bypass spaces 62 for tendons 50 and coil pipes 48 that control more distal segments 28 or tip 14, and that bypass vertebra-type control ring 54 and the present segment 28. These coil pipe bypass spaces 62, in this variation of the vertebrae-type control ring 54, preferably conform to the outer diameter of coil pipes 48. The number of coil pipe bypass spaces 62 vary depending on the number of tendons, and, therefore, the number of coil pipes needed to articulate all the segments 28 and steerable distal portion 14. It will be appreciated that not all vertebrae-type control rings 54 of a particular segment 28 need to have coil pipe bypass spaces 62. As described further below, intermediate vertebra-type control rings 54' (FIG. 4C) between segments need not have coil pipe bypass spaces 62, rather the coil pipes can simply pass through the lumen formed by central aperture 56'. In this alternative, the lumen formed by central aperture 56' house the various access lumens, working channels, light channels, air and water channels, vacuum channels, as described above, as well as coil pipe/tendon combinations that do not control that particular segment.

Figure 4D:
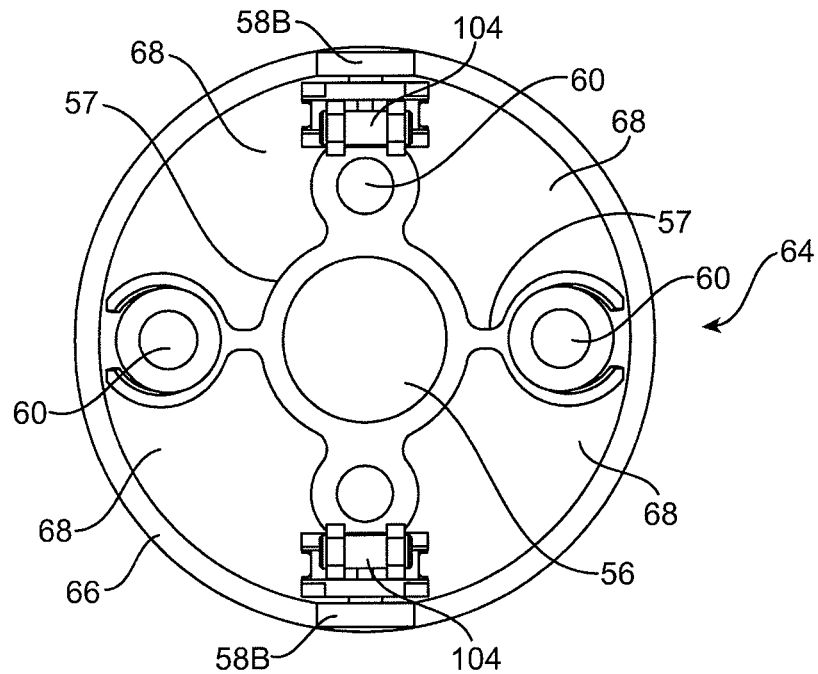
Figure 4E:
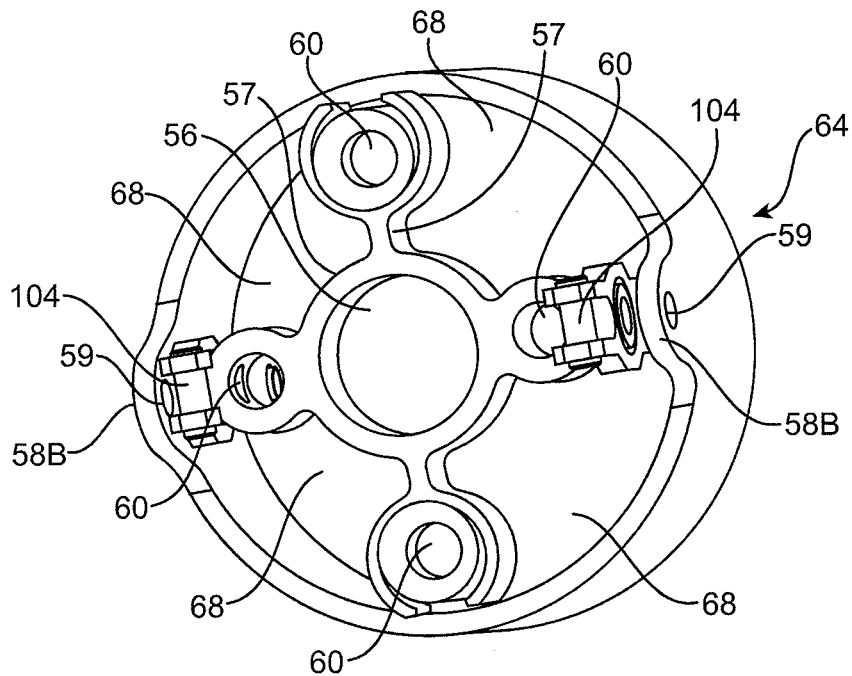

FIG. 4D-E show another variation of vertebra-type control ring 64 in sectional and perspective views. In FIG. 4D-E, tendons 50 and coil pipes 48 that bypass a segment may be contained within body 66 (FIG. 4D) of vertebra-type control ring 64 in an alternative coil pipe bypassing space or quadrant 68, rather than the scallops 62 along the outer edge of vertebra-type control ring 54 as previously described. Quadrants 68 are the preferred way to handle coil pipes 48 that must by-pass a segment. Vertebra-type control ring 64 of FIG. 4D-4E show four coil pipe bypassing spaces/quadrants 68, but more or fewer may be used. It will be appreciated that cross bar 57 can pivot at hinge points 59 in one embodiment or may fixed relative to body 66. Other aspects of this variation of vertebra-type control ring are similar to that described above and are, accordingly, called out with the same reference number. It is noted that tie-off rods 104 can be used to tie off the distal ends of tendons 50 in this embodiment.

Figure 4F:
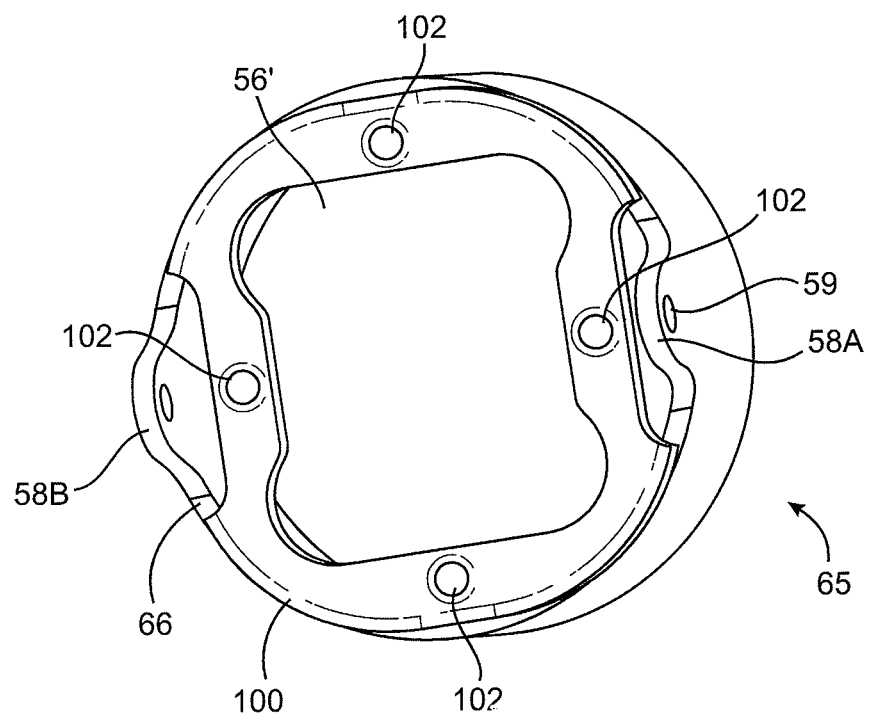

The skilled artisan will appreciate that coil pipes 48 by-passing a vertebrae via quadrants 68 will define an approximately cylindrical coil pipe containment space roughly defined by the outer diameter of vertebrae-type control ring 64. This space is loosely defined by the grouped coil pipes as they pass through and between the vertebrae. As described more thoroughly below, it is possible and preferred to have intermediate vertebra-type control rings without coil pipe bypassing spaces, as shown in vertebra-type control ring 54' (FIG. 4C) or 65 (FIG. 4F). In either construction, central aperture 56 or 56' of the control rings collectively forms a lumen (not shown) through which channels and cables necessary or desired for the endoscope function pass, as well as coil pipes and tendons by-passing that particular segment. Preferably, more proximal segments will have larger diameter vertebrae in order to provide larger quadrants 68 or central aperture 56 or 56' to accommodate a larger number of coil pipes 48 that must reach the more distal segments 28 and tip 14. The more distal segments 28 and steerable distal portion 14 can be constructed with vertebrae-type control rings 64 or 65 having a smaller diameter, thereby making the distal portions of elongate body 12 have a smaller diameter. While this is preferred, the skilled artisan will recognize that any diameter vertebrae may be used limited only by the need to accommodate the coil pipes and tendons necessary to articulate segments 28 and steerable distal portion 14 of the endoscope.

Referring again to FIG. 5, coil pipes 48 are fixed at their distal and proximal ends between actuators 60 and the proximal end of segment 28 under control by those actuators. FIG. 5 shows only one segment 28 (which, as discussed, could also be steerable distal portion 14), and, for clarity, the other parts of a complete endoscope have been omitted from FIG. 5. When tendons 50 are placed under tension, the force is transferred across the length of segment 28; coil pipes 48 provide the opposite force at the proximal end of the segment being articulated in order to cause the articulation. This force is, primarily, a compression force or axial loading transferred along the length of the coil pipe where it is fixed between the actuator and the proximal end of the segment being articulated. A preferred embodiment of the present invention utilizes one actuator per tendon, and utilizes four tendons per segment, as described above, although only one actuator 60 is depicted for clarity. Details relating to actuator 60 and connecting actuator 60 to tendons 50 are described in U.S. patent application Ser. No. 10/988,212, previously incorporated by reference.

The skilled artisan will appreciate that articulation of multiple segments 28 along the length of elongate body 12 will require that many coil pipes 50 extend down the length of elongate body 12 and through coil pipe by-passing spaces, with the number decreasing by four coil pipes (in this example) at the proximal end of each segment. Thus, a 17 segmented elongate body (16 segments 28 and 1 tip 14) requires 68 coil pipes going into the proximal end of elongate body 12, which decreases by four coil pipes for each distally adjacent segment 28 (assuming one uses four tendon/coil pipes combinations per segment as in the present example). It also requires the actuation or tensioning of 68 tendons, with four tendons terminating at the distal end of each segment. This requires 68 actuators in this preferred embodiment, one actuator per tendon 50.

The skilled artisan will also appreciate that there is not a one to one correspondence between the force applied by actuators 60 at the proximal end of tendons 50 and the force realized at the distal end of tendons 50 to articulate segment 28. When elongate body 12 is in its substantially straight configuration, friction between tendons 50 and coil pipes 48 results in frictional losses along the length of the coil pipe while applying tension to articulate a segment or the tip. Articulation of segments 28 and steerable distal portion 14 results in further losses and inefficiencies for many reasons. For example, and without limitation, when elongate body 12 articulates (for example at the Sigmoid colon during a colonoscopy procedure), coil pipes 48 must move longitudinally along elongate body 12 to either "gain" or "lose" length depending whether coil pipes 48 are on the inner or outer portion of the bend created by the articulation. As described above, an embodiment of the present invention provides quadrants 68 or coil pipe by-passing spaces 62 that permit the passage of coil pipes 48 along elongate body 12 until they reach the proximal portion of the segment they control. The "gain" or "loss" of coil pipe length requires coil pipes 48 to slide up and down elongate body 12 and within quadrants 68 or coil pipe by-passing spaces 62 creating further frictional losses by virtue of friction between the coil pipes and/or between the coil pipes and the vertebra. There is also the additional friction created between a coil pipe and a tendon by virtue of the bend.

Frictional losses caused by the coil pipe/tendon bending (by virtue of a segment bending) reduce the working force available to articulate segments. The frictional loss is dependent on the material coefficient of friction and the accumulated bend (total tortuosity) of the coil pipe/tendon as elongate body 12 moves through a tortuous path. Total tortuosity is the amount of accumulated bend along the length of a coil pipe, which is closely approximated by the amount of accumulated bend along the length of that portion of elongate body 12 through which the coil pipe travels. For example an S-bend through the Sigmoid colon would contribute approximately 2×90° or 180° to the total tortuosity. As a segment bends coil pipes/tendons within that segment will also bend. The tendon tension applies a normal load towards the center of curvature of the coil pipe, as depicted in FIG. 6 that graphically depicts a coil pipe going through a 180 bend around a column.

Figure 6:
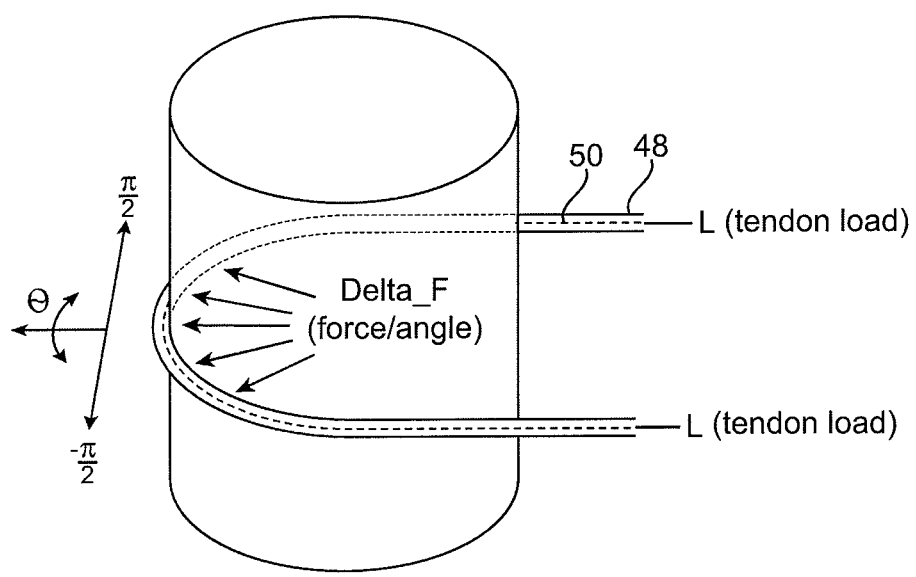
FIG. 6 provides a graphic for explaining static radial frictional forces between tendons and coil pipes in an embodiment of the present invention where the coil pipes are not spiraled.

Referring to FIG. 6, the static friction for coil pipes extending down the length of elongate body 12 can be represented by the following balanced equations, where $\theta$ is the total tortuosity. Delta_F is constant with a given load L on either tendon. Note there are at least three sources of friction: (1) friction between the tendons and the coil pipe; (2) friction between the coil pipes and the ring structures; and (3) friction between the individual coil pipes.

$$\int_{-\pi/2}^{\pi/2} \text{Delta\_F} * \cos(\theta) d\theta = 2*L; \text{ (units of Delta\_F are in force/angle)}$$

$$\text{Delta\_F} * [\sin(\pi/2) - (\sin(-\pi/2))] = 2*L;$$

$$\text{Delta\_F} * [1 - (-1)] = 2L$$

$$\text{Delta\_F} = L$$

Having found Delta_F, the general normal cable loading is $F_N$=Delta_F*θ=L*θ. The static radial friction is, therefore, $F_r(θ)=F_N*μ$=Delta_F*θ*μ=L*θ*μ (μ is coefficient of friction). Note that this equation has been solved for an ideal, hypothetical situation where the coil pipe is bent around a hypothetical column and static equal load is place at either end of the tendon going through the coil pipe. The same analysis applies for the static friction between a coil pipe and ring structures of a segment, where L is the given external load on the coil pipe. The solution is the same, but will have different loads (L) and different coefficients of friction (μ). This is a reasonable model to assess the static frictional loads for a coil pipe going through a segment comprised of vertebra-type ring structures having a total tortuosity of θ. Therefore, the static friction force for 180 degrees of accumulated tortuosity (two ninety degree bends or an S-bend, for example) is $F_r(π)=π*L*μ$. The calculation for brake free forces and dynamic resistance loads is more complicated but can also be solved with an exponentially decaying resistance load.

Figure 7A:
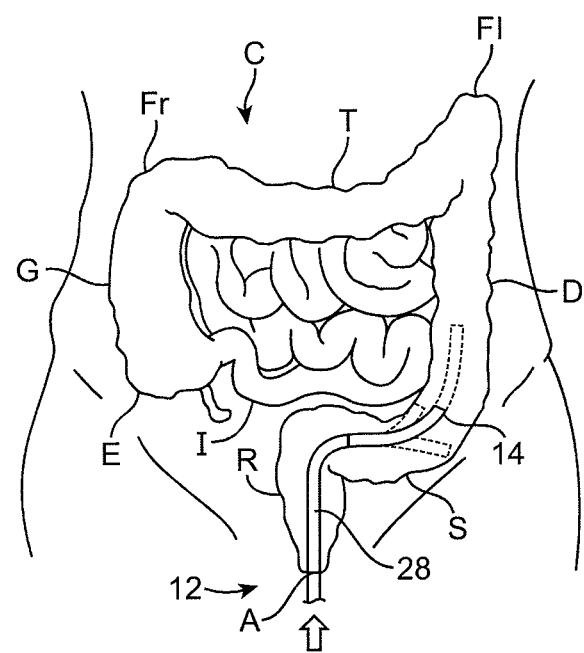
FIG. 7 depicts a schematic of advancing an endoscope in a colon in accordance with an embodiment of the present invention.
Figure 7B:
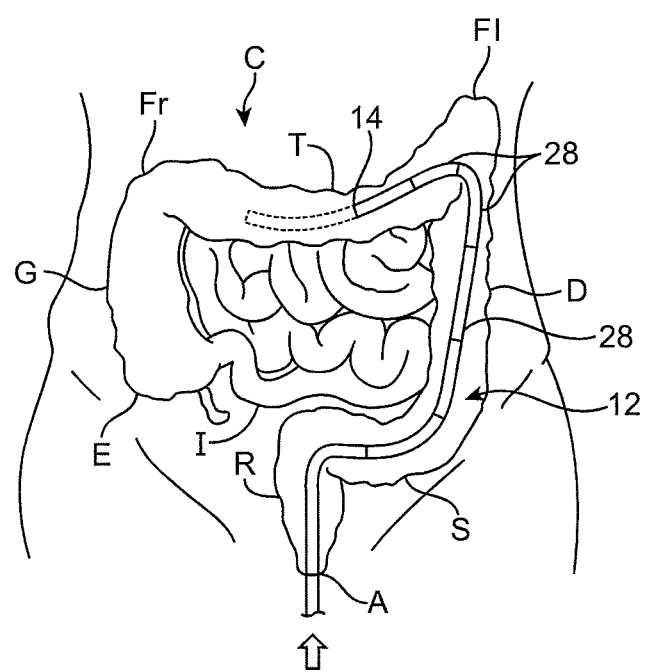

Additionally, but related, elongate body 12 may enter more than one tortuous bend simultaneously. Referring to FIG. 7A-B, this occurs when, for example and without limitation, performing a colonoscopy with an embodiment of the present invention elongate body 12 must move through a highly tortuous path. Electronic controller 30, in a preferred embodiment, controls the articulation of each segment 28 to take the shape of adjacent segments or tip as elongate body 12 is advanced through a tortuous path, such as the colon. Referring to FIG. 7A, a user articulates steerable distal portion 14 to select a desired path, through the Sigmoid colon S for example (an approximate S-bend or 180 degrees of total tortuosity), and then advances the endoscope through the anus A. Electronic controller 30 knows the shape of segments 28 and steerable distal portion 14 prior to the advancement of elongate body 12 into the colon, as described more thoroughly in U.S. patent application Ser. No. 11/019,963, previously incorporated herein by reference. Electronic controller 30 causes adjacent segments to adopt the shape of the segment or steerable distal portion immediately preceding it. Therefore, upon advancing elongate body 12 through the colon C, electronic motion controller 30 will maintain the approximate tortuous S-shape of the Sigmoid colon S in elongate body 12 by automatically controlling segments 28 to adopt the approximate shape of the immediately preceding segment. This follow-the-leader technique is further described in U.S. patent application Ser. No. 11/019,963, previously incorporated herein by reference. As described above, coil pipes 48 need to slide along elongate body 12 to accommodate the "gain" or "loss" of coil pipe length resulting from the articulation of elongate body 12. Recall from the equation above that the frictional force is proportional to both total tortuosity and the material coefficient of friction. There are two coefficients of friction of interest, one for the tendon against the internal lumen of the coil pipe, and the other for the coil pipe against the vertebra-type ring structures.

Referring to FIG. 7B, when steerable distal portion 14 of elongate body 12 enters into a second tortuous bend, at the splenic flexure F1 of the colon for example, coil pipes 48 need to accommodate the "gain" or "loss" of coil pipe length for both the new bend in the splenic flexure F1 and for the first S-bend at the Sigmoid colon S. As the user advances elongate body 12 into the transverse colon T electronic controller 30 continues to maintain the bends at the splenic flexure F1 and the Sigmoid colon S. However, coil pipes 48 need to slide the entire length of elongate body 12 (as described above), including through the first tortuous proximal bend in the Sigmoid colon S, and the second tortuous more distal bend in the splenic flexure F1 to accommodate for the "loss" and "gain" of coil pipe length.

Figure 8:
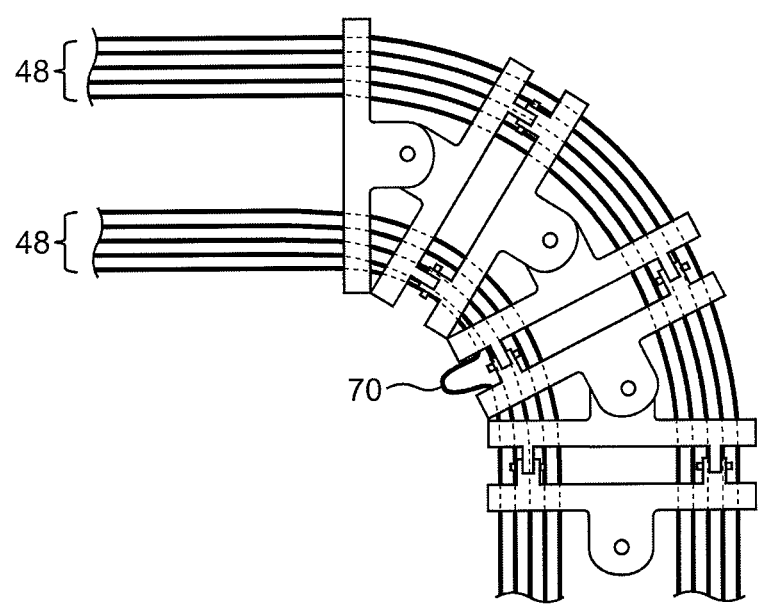
FIG. 8 depicts a schematic of an undesirable bell-shape bend of a coil tube.

It was found that coil pipes 48 did not have the ability to slide along the length of elongate body 12 when in such a tortuous state. Without wishing to be bound by any particular theory, the inventors believe that the frictional forces between the coil pipes and the vertebra-type ring structures bind the coil pipes and they are unable to slide along the length of elongate body 12. Referring to FIG. 8, catastrophically the coil pipe exits the coil pipe containment boundary (discussed previously) in a severe bell-curve type shape 70, or adopts severe bends (not shown) within the coil pipe containment boundary. This bell-curve bend 70 and/or other severe bends in coil pipes 48 dramatically increases friction between coil pipes 48 and tendons 50, and also stiffens the segments requiring greater forces to achieve the desired articulation than would otherwise be required without the bell-curve or other severe bends in the coil pipes. As the segments having bell-shape curve 70 and/or other severe bends in coil pipe 48 straighten, the excess coil pipe length is no longer required to accommodate the bend in that particular segment of elongate body 12. Therefore, coil pipe 48 moves back into the coil pipe containment area and/or the other severe bends begin to straighten as the bend in segment 28 begins to straighten, but in doing so coil pipe 48 frequently herniates. The skilled artisan will appreciate that herniation of the coil pipe can be caused by a variety of mechanisms. Moreover, the skilled artisan will appreciate that bell-curve shape 70 or other severe bends can occur anywhere along the length of elongate body 12, and the location of such bends is not limited to the bending segments. A herniation, as will be described more fully below, is a permanent or plastic lateral deformation of the coil pipe. The primary cause of a herniation is believed by the inventors (without wishing to be bound by any particular theory) to be the result of the coil pipes binding (i.e. inability to slide or significantly reduced ability to slide) along the length of elongate body 12.

Figure 9A:
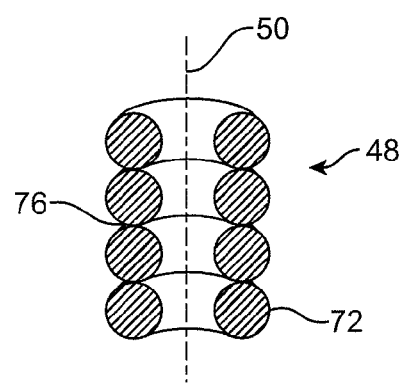
FIG. 9 depicts an embodiment of a coil pipe made with circular cross-section wire and a herniation of the coil pipe.
Figure 9B:
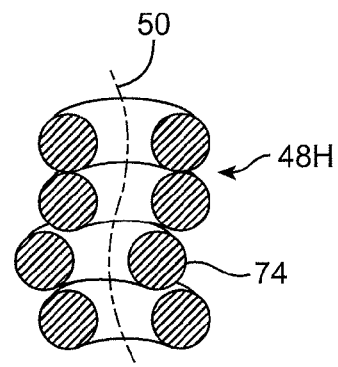

Referring to FIG. 9, coil pipes 48 are typically made of circular cross-section high tensile strength wire 72 wound in a tight coil to form a hollow pipe-like structure. The larger the tensile strength the more difficult it will be to make the material plastically deform. In a preferred embodiment high tensile 302, 303 or 304 VT SST was specified with a tensile strength greater than about 40,000 PSI. In a herniated coil pipe 48H (FIG. 9B) at least one of the coils 74 is permanently, laterally displaced, thereby significantly decreasing the effective diameter through which tendon 50 may pass. This results in a concomitant catastrophic increase in the frictional losses caused by friction between the coil pipe and the tendon passing therethrough. This lateral displacement also significantly reduces column strength of the coil pipe, thereby significantly reducing the ability to articulate a segment. In addition to significantly reducing the amount of force delivered by tendon 50 to articulate the segment or tip, the additional friction will prematurely wear out tendon 50.

Without wishing to be bound by any particular theory, the inventors believe that the coil pipes rubbing on the vertebrae (or other ring structure) as the coil pipes re-enter the coil pipe containment area or otherwise straighten cause lateral forces on the coil pipes, which cause the coil pipes to resist axial movement or bind leading them to herniate. The inventors further hypothesize, again without wishing to be bound by any particular theory, that the ridges 76 (FIG. 9A) of the coiled wire 72 bump along the vertebrae or ring structure as the coil pipes re-enter the coil pipe containment area or otherwise straighten creating additional forces on the coil pipe structure. This is further exacerbated, again without being bound by any particular theory, by the bell-shaped curve or other severe bends separating the coils similar to the bending of a spring, thereby making the ridges more pronounced.

Figure 10:
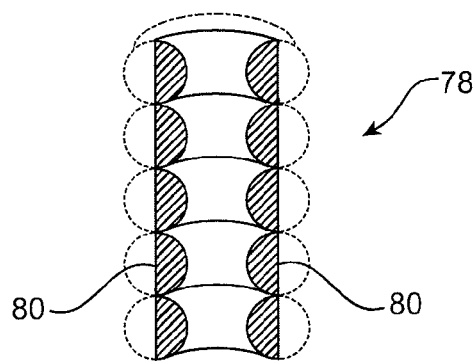
FIG. 10 depicts a centerless ground coil pipe in accordance with an embodiment of the present invention.

FIG. 10 depicts an embodiment of centerless ground coil pipe 78 in accordance with an embodiment of the present invention. As described above coil pipes 48 slide along the length of elongate body 12 as segments 28 articulate along a tortuous path. Adding lubricity between coil pipes 48 is, therefore, desired. However, using a lubricant, such as oil or other substance, is not highly desired because, at a minimum, the lubricant wears out making more frequent service of the endoscope necessary. Centerless ground coil pipe 78 is essentially the same as coil pipe 48 described above, but approximately half the diameter of coil wire 72 (shown in shadow) on either side of centerless ground coil pipe 78 is ground away or removed to create the centerless ground coil pipe 78. The opposing flat sides 80 provide increased lubricity between coil pipes as they slide up and down elongate body 12, and also provide increased lubricity as "excess" coil pipe length slides back into the coil pipe containment area or otherwise straightens. The skilled artisan will appreciate that any appropriate lubricant may also be used in combination with the centerless ground coil pipes, although this is not preferred. The inventors found that this solution did not sufficiently resolve the binding and ultimate herniation of the coil pipes. The inventors hypothesize that the design is sound, but the less preferred outcome of the solution resulted from the difficulty in reliably manufacturing centerless ground coil pipes with substantially opposing substantially flat sides.

Figure 11A:
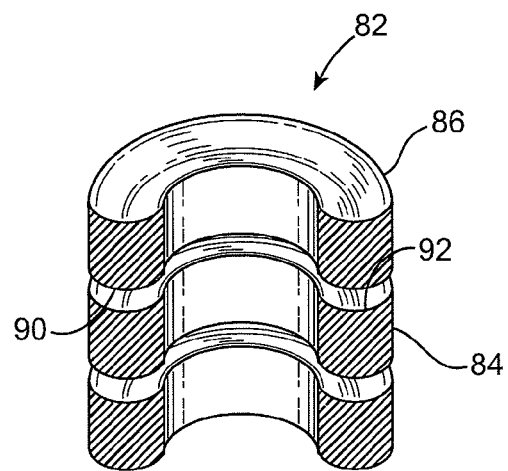
FIG. 11 depicts a coil pipe made with "D-shaped" wire in accordance with an embodiment of the present invention, and various embodiments of how to make "D-shaped" wire.
Figure 11B:
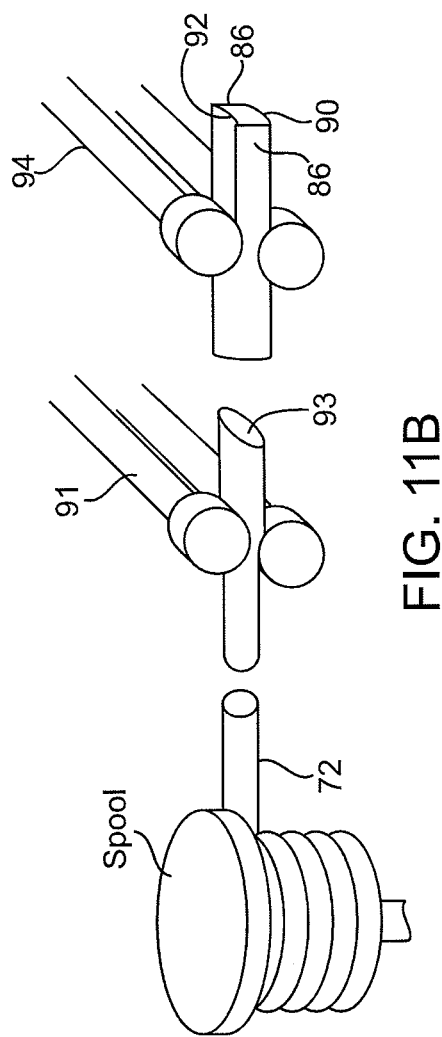
Figure 11C:
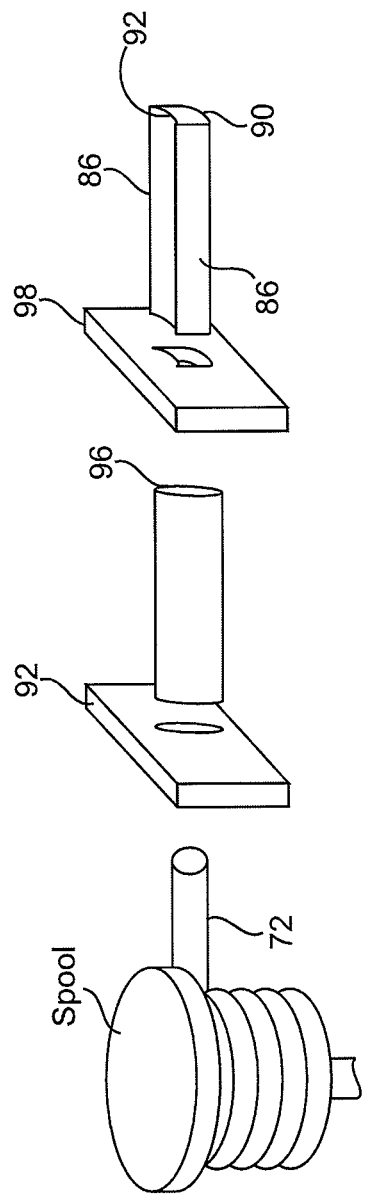

In accordance with an alternative embodiment of the present invention FIG. 11A depicts D-shaped coil pipe 82 made from D-shaped wire 84. In this embodiment convex portion 90 of D-shaped wire approximately nests in concave portion 92 of D-shaped wire (FIG. 11A). D-shaped wire 84 can be manufactured in a number of ways as will be appreciated by the skilled artisan. In one embodiment, referring to FIG. 11B, round wire 72 is rolled by first roller 91 or "Turkshead die" into an approximate oval shape 93 and the wire is rotated approximately 90 degrees and fed into second roller 94 or "Turkshead die." Second roller 94 creates the concave shape 92 and convex shape 90 at opposite ends of the parallel substantially flat sides 86 created by first roller 91. Alternatively, D-shaped wire can be formed by extrusion or by pulling a fully annealed or soft wire through one or more dies as shown in FIG. 11C. First, wire 72 is pulled through die 92 to obtain an approximately oval shaped wire 96. Oval shaped wire 96 is then pulled through die 98 to provide the concave shape 92 and convex shape 90 at opposite ends of the parallel substantially flat sides 86. The wire is then hardened to hold a set shape as in a coil pipe. The skilled artisan will appreciate that dies 95 and 98 can be a single die and that orientation of the die or rotation of the wire is a matter of manufacturing choice. This would also be true with the orientation of first and second rollers discussed above.

Figure 11D:
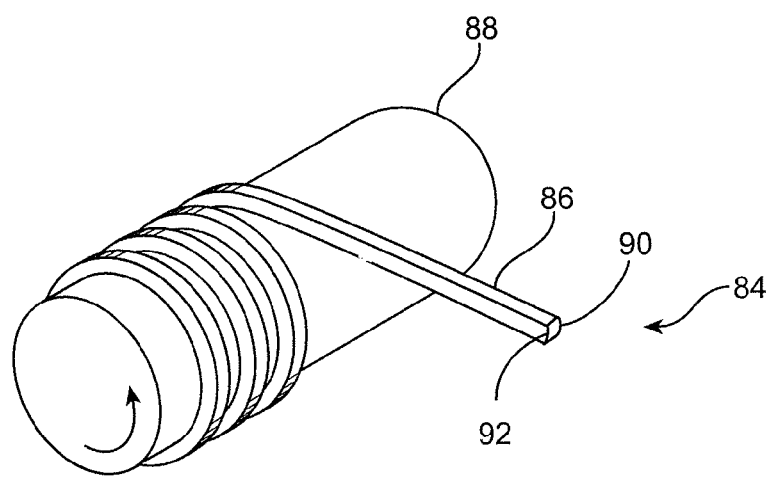

Manufacture of D-shaped coil pipe 82 with D-shaped wire is similar to the manufacture of coil pipe made with circular wire. Referring to FIG. 11D, the main difference is that D-shaped wire 84 needs to be oriented with one of the flat sides 86 against mandrel 88. Preferably, the convex portion 90 of the "D" approximately nests into the concave portion 92 of the "D" as the D-shaped wire is wound onto the mandrel to form the coil pipe.

Figure 11E:
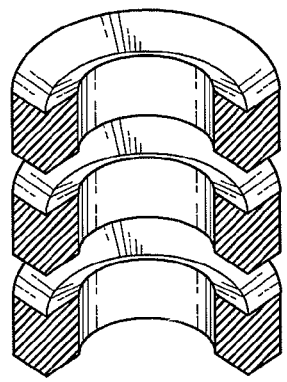
Figure 11F:
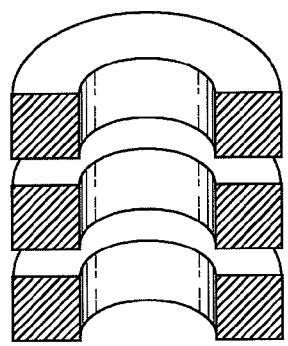

Nesting convex portion 90 into concave portion 92 provides for a higher surface area contact between wires of each coil than a coil pipe manufactured with circular cross section wire, particularly when the coil pipe is under compressive stresses. Additionally, the sides of convex portion 90 and concave portion 92 provide resistance against herniation upon application of lateral forces. Like the centerless ground coil pipe 78, D-shaped coil pipe 82 also provides increased lubricity by virtue of substantially flat portions 86 of D-shaped coil pipe 82. D-shaped coil pipe 82 worked better than centerless ground coil pipe 78 in preventing herniations, and is therefore more preferred over centerless ground coil pipe 78. Additionally, the manufacturability of D-shaped coil pipe 82 is more consistent than that of the centerless ground coil pipe 78, which adds to the preference of D-shaped coil pipe 82. Furthermore, orienting coil pipe 48 to grind off or flatten the sides to achieve centerless ground coil pipe 78 can prove challenging, as discussed above. The skilled artisan will appreciate that shapes of wire other than D-shaped may be used in accordance with the present invention. For example the concave and convex portion of D-shaped coil pipe 82 may have any geometrical shape that can nest together. These may include, without limitation, V-shaped coil pipe 94 (FIG. 11E). Furthermore, an alternative embodiment, though not preferred, could be square or rectangular cross-section wire oriented to have flat sides against each other, as shown in FIG. 11F, which also will provide resistance against herniation upon application of lateral forces. Additionally, a benefit of using Bowden-type cables made from coil pipes is that they are flexible even when under compressive load. D-shaped coil pipes also remain very flexible under high compressive loads.

Figure 12:
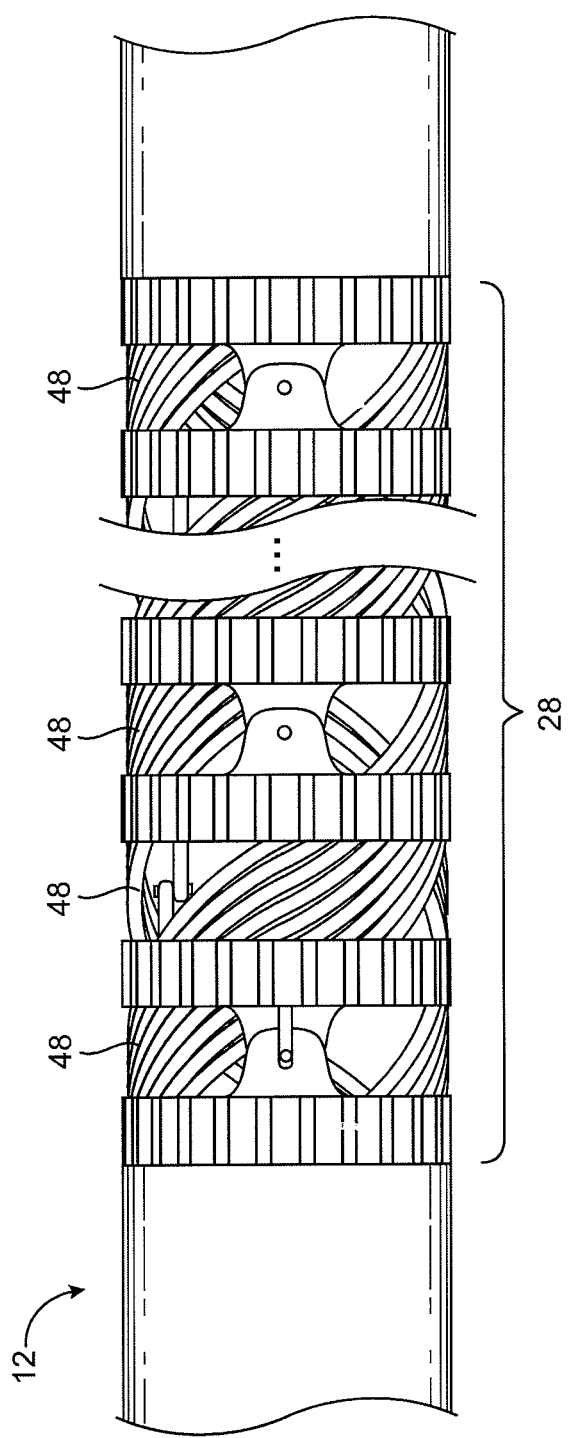
FIG. 12 depicts an illustration of coil pipe spiraled along a segment in accordance with an embodiment of the present invention.

FIG. 12 depicts a preferred alternative embodiment for managing the coil pipes that reduces or eliminates the herniation problem by reducing or eliminating the need for the coil pipes to slide along the entire length of elongate body 12. As described above, coil pipe 48 must slide up or down the entire length of elongate body 12 to accommodate a bend in a segment. Referring to FIG. 12, spiraling coil pipes 48 along elongate body 12 and segments 28 significantly reduces and effectively eliminates the herniation problems identified above. Without wishing to be bound by any particular theory, the inventors hypothesize that the spiraled coil pipe localizes the movement or slacking of the coil pipes to an area at or close to the segment undergoing articulation. Therefore, again without wishing to be bound by any particular theory, when a segment articulates the spiraled coil pipe moves within or near a segment locally, thereby reducing or eliminating the need for the coil pipe to slide up or down the entire length of the elongate body. An analogy, again without wishing to be bound by any particular theory, would be a rope or cable made of spiraled strands bending over a pulley; the gain and loss of length of the individual strands in the rope takes place locally at the point of the bend around the pulley, because the strands alternate from the outside to the inside of the bend; the inside strand section gives what the outside strand needs.

The inventors observed that the spiraled coil pipes did not exit the coil pipe containment area in bell shaped curves or exhibit other extreme bends as described above, and they observed little to no herniation of the coil pipes. Spiraling the coil pipes will reduce or prevent herniation with D-Shaped, centerless ground or circular wire coil pipes as well. However, circular wire coil pipes are preferred for ease of manufacturing reasons.

The main benefit with using a spiraled structure identified by the inventors is reduced friction between a coil pipe and vertebra-type ring structures by virtue of the elimination or reduction of sliding of the coil pipes along the elongate body. There is a relatively smaller increase of frictional forces resulting from the increase of overall length of coil pipe through which a tendon must pass, and an increase of overall tortuosity as a result of spiraling the coil pipes along elongate body 12.

Figure 13:
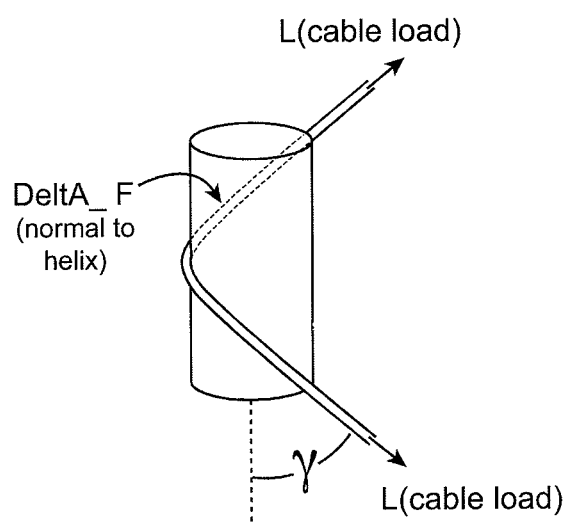
FIG. 13 provides a graphic for explaining static radial frictional forces between tendons and coil pipes in an embodiment of the present invention where the coil pipes are spiraled.

The static friction from a spiral loading differs from that of radial loading described above. Tendon tension, as described for radial loading, applies a normal load toward the center of curvature and results in static radial friction of $F_r(n) = \mu * L * \mu$ for 180 degrees of total tortuosity. Static radial loading for a spiraled coil pipe can be solved and calculated in the same fashion. It is noted that because, as hypothesized by the inventors, spiraling localizes coil pipe movement to a segment undergoing a bend friction for coil pipes sliding against vertebra-type ring structures is reduced or eliminated. Referring to FIG. 13, cable load L is assumed to be the same at both ends of the spiral. Balanced equations follow, where γ is the spiral angle and θ is, again, total tortuosity, which as noted is increased by virtue of the spiral:

$$\int_{-\pi/2}^{\pi/2} \text{Delta\_F} * \cos(\theta) d\theta = 2 * L * \sin(\gamma);$$

units of Delta_F are in force/angle $$\text{Delta\_F} * [\sin(\pi/2) - (\sin(-\pi/2))] = 2 * L * \sin(\gamma);$$

$$\text{Delta\_F} * [1 - (-1)] = 2 * L * \sin(\gamma)$$

$$\text{Delta\_F} = L * \sin(\gamma)$$

Having found Delta_F the general normal cable loading is $F_N = \text{Delta\_F} * \theta * \sin(\gamma) = L * \theta * \sin(\gamma)$. The static radial friction is, therefore, $F_r(\theta) = F_N * \mu = \text{Delta\_F} * \theta * \sin(\gamma) * \mu = \mu * L * \theta * \sin(\gamma)$. Note that this equation has been solved for an ideal, hypothetical situation where the coil pipe is spiraled around a hypothetical column 180° and static equal load is place at either end of the tendon going through the coil pipe. This is a reasonable model to assess the static frictional loads for a coil pipe spiraling through a segment comprised of vertebra-type ring structures. It must be recalled, however, that total tortuosity is now increased as a result of the spiraling.

Total tortuosity is the sum of all angles of bends in a coil pipe from its proximal end assuming the coil pipes are not spiraled along the elongate body. However, as will be appreciated, the spiral angle γ adds to the total tortuosity, but under larger (high degree of) bends of a segment the amount of tortuosity added by for small spiral angles (γ) is approximately the same as that of a non-spiraled embodiment undergoing the same multiple bends, so long as the spiraling is not excessive. Excessive spiraling with large spiral angle γ or wrapping the coil pipe too many times around a segment has a deleterious affect for several reasons. One reason is that the increased number of wraps dramatically increases the length of the coil pipe, thereby increasing the friction between the coil pipe and the tendon. More importantly, the overall tortuosity θ increases to an unacceptable level with the increased number of wraps (which proportionally increases the static friction) and spiral angle, i.e., friction added ($F_r \approx * L * \theta * \sin(\gamma)$) increases directly with spiral angle. The inventors reasoned that too much spiraling would result in the detriment of increased friction by virtue of the increase of total tortuosity (θ) out weighing the benefit of reducing or eliminating binding. Numerically the inventors determined that a single 360 degree spiral, or approximately one wrap along each segment is the preferred amount of spiraling. It was determined empirically and numerically that approximately one 360 degree spiral wrap per segment of approximately 10 cm along the elongate body reduced or eliminated the need for the coil pipe to slide between segments to accommodate a bend, thereby reducing or eliminating herniation, and that this benefit far outweighed any increase of friction resulting from the amount of tortuosity added by the spiraled coil pipes. It was also determined numerically that an integral number of spiral wraps was preferred to ensure localization of coil pipe movement during the bending of a segment. The skilled artisan will appreciate the amount of spiraling or wraps used will depend on the system and the purpose for which the system will be used. It will also be appreciated that the spiral angle (γ) need not be constant along the length of a segment.

Figure 15A:
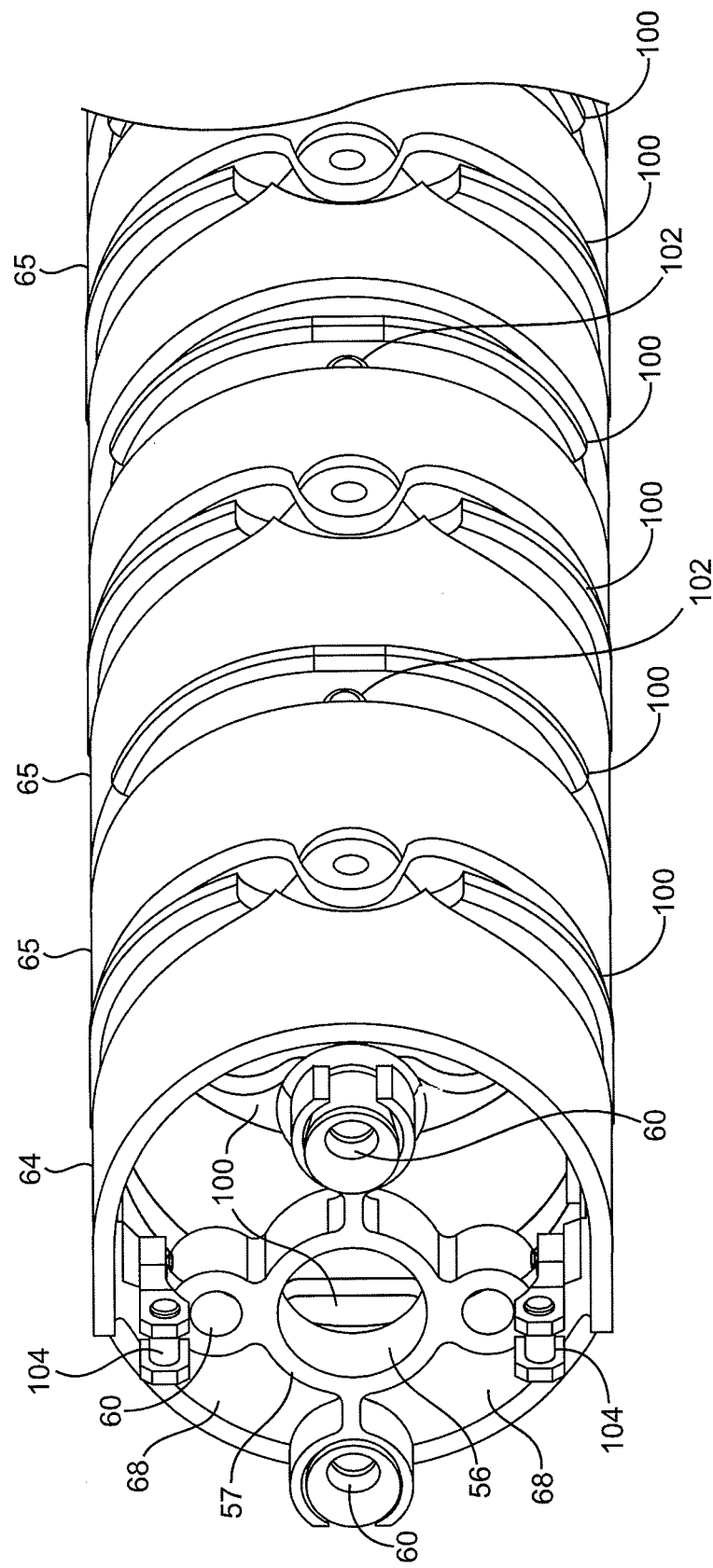
FIG. 15 depicts an alternative embodiment of a steerable distal portion or a controllable segment.

Referring back to FIG. 4D-F, in an embodiment of the present invention, quadrants 68 of vertebrae type control ring 64 are used to maintain coil pipes 48 spiraled along elongate body 12. In this embodiment more than one vertebra-type control ring 64 in a segment has quadrants 68, and the coil pipes are passed through the quadrants to established the preferred approximately one spiral wrap per segment. In another preferred embodiment, referring briefly to FIG. 15A, distal (not shown) and proximal vertebrae-type control rings 64 of each segment have quadrants 68, and intermediate vertebrae-type control rings 65 do not have quadrants 68. In this preferred embodiment the quadrants are approximately longitudinally aligned, and coil pipes are passed through the aligned quadrants after spiraling within the intermediate control rings 65 to achieve the preferred approximately one spiral wrap. It will be appreciated that the number of coil pipes passing through the quadrants will be equally divided between the quadrants, although other configurations can be used. The skilled artisan will appreciate that many different configurations and mechanisms may be used to maintain the spiral along the length of elongate body 12.

Referring to FIG. 14, coil pipes 48 are routed through quadrants 68 (not shown) in proximal vertebra-type control ring 64 in segment 28, through vertebra-type control rings 65 without quadrants in that segment, through quadrants 68 (not shown) in distal vertebra-type control ring 64 in that segment. The working channel, fiber optics cable, suction channel, video cable and the like (not shown) are routed through central opening 56 of vertebra-type control rings 64 and through the lumen (along with the coil pipes) created by intermediate vertebra-type control rings 65 without quadrants. The vertebrae 64 with the quadrants are then rotated relative to each other to achieve the amount of desired spiraling of the coil pipes, the rotation being depicted graphically in FIG. 14B. Hinging of the vertebrae will maintain the spiral, as will be appreciated by the skilled artisan. As noted, approximately a full spiral wrap of 2π per segment 28 is preferred, but the skilled artisan will appreciate that the number of wraps will depend on the purpose for which the device will be used. As will also be appreciated, only four coil pipes are depicted with the other details of the segments and endoscope being omitted from FIG. 14 for purposes of clarity. It is noted that the skilled artisan will appreciate many different configurations of vertebra-type control rings with and without quadrants can be used to achieve the desired spiraling.

As noted, at least one vertebra control ring 64 with quadrants 68 is used per segment and preferably two to maintain the preferred spiral structure of the coil pipes by-passing that segment, and that the remaining vertebra-type control rings of that segment do not have quadrants. As discussed above, central opening 56 of vertebra-type control ring 64 provides a location for passing working channels, optical cables and the like through vertebra-type control ring 64 and quadrants 68 provide a separate by-pass space for coil pipes not controlling articulation of that particular segment, and for maintaining the spiral structure of the coil pipes. The remaining control rings 65 of a segment have no by-pass space. Rather, the coil pipes, the working channel, air line, water line, suction line, optical cables and the like all pass through the central lumen created by central opening 56' (FIG. 4F) of vertebra-type control rings 65 by aligning vertebra-type control rings 65, and are not separated by quadrants 68 as in vertebra-type control rings 64.

Figure 15B:
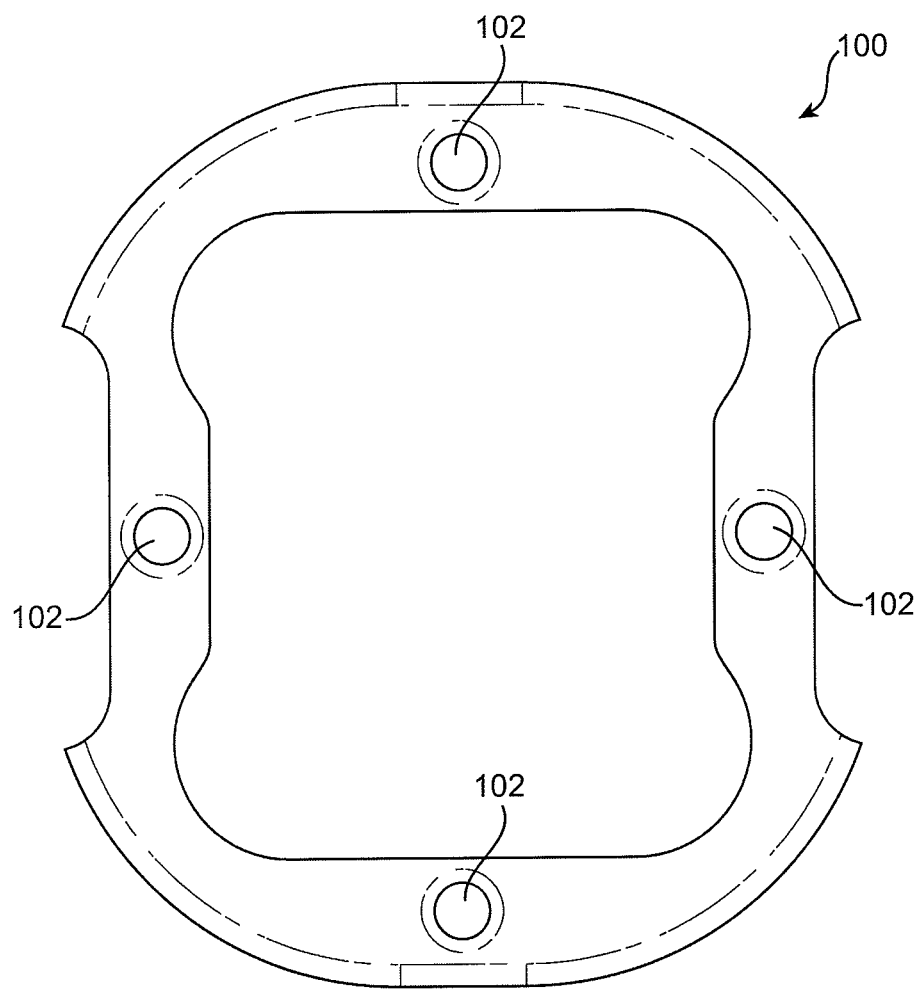

Referring again to FIG. 15, tendons 50 controlling a particular segment are kept separate from the spiraled coil pipes, the working channel, air line, water line etc. by intermediate ring structures 100 attached at the hinge between control rings 65 not having quadrants 68. These intermediate ring structures 100 (FIG. 15B) are situated between vertebra control rings 65. Four holes 102 are shown in ring structure 100 through which tendons 50 controlling articulation of that segment run. More holes may be used per tendon depending on how force is applied to the segment via the tendon(s), and the total number of holes depends on the number of tendons 50 used to control the segment, tour in this example. In the proximal vertebra-type control ring 64 having quadrants 68, holes 60 are where coil pipes controlling that segment terminate and are fixed. As described above, tendon 50 extends out of the coil pipe and along the segment through holes 100 and then terminate at the distal end of the segment at tie off rods 104 of the distal vertebra-type control ring 64. The skilled artisan will recognize that tendon 50 controlling a particular segment need only terminate somewhere within that segment such that force can be effectively transferred to and along that segment to effect articulation.

This preferred embodiment has the advantage of, at least, (1) spiraling the coil pipes along the length of the elongate body, as described above, and (2) providing relatively unconstrained space in vertebra-type control rings 65 without quadrants 68 intermediate to vertebra-type control rings 64 having quadrants 68, such that coil pipes can move locally and relatively unconstrained to accommodate articulation of that particular segment. The inventors believe, again without wishing to be bound by any particular theory, that this permits the coil pipes to move locally and accommodate the bend in a segment without having to slide the entire length of the elongate body, thereby not binding the coil pipes and the concomitant reduction or elimination of herniations in the coil pipes.

The skilled artisan will appreciate there are many different ring structures and many different ways to achieve the desired spiral structure of coil pipes. For example, and without limitation, the coil pipes could be spirally arranged in scalloped by-pass spaces 62 in the outer edge of vertebra-type control ring 60 (FIG. 4A-B), although this is less desirable because it moves the coil pipes further away from the desired longitudinal centerline of elongate body 12, and these spaces have more friction than when the coil pipes are passed through quadrants 68 or the center 65 of vertebrae. Additionally, the skilled artisan will appreciate that quadrants 68 can exist in more than one vertebra-type control ring 64 within a segment, and that more or fewer than four quadrants can be used. The skilled artisan will appreciate how to orient quadrants on one vertebra relative those on an other vertebra(e) having quadrants within a segment and along the elongate body to achieve the desired spiral arrangement of coil pipes.

The foregoing description, for purposes of explanation, used some specific nomenclature to provide a thorough understanding of the invention. Nevertheless, the foregoing descriptions of the preferred embodiments of the present invention are presented for purposes of illustration and description and are not intended to be exhaustive or to limit the invention to the precise forms disclosed; obvious modification and variation are possible in view of the above teachings.

What is claimed is:

1. A system for managing the transmission of force to articulate an elongate medical device, the system comprising:
an elongate body comprising a plurality of articulatable segments;
a plurality of coil pipes, wherein each coil pipe is fixed at a proximal end of each coil pipe relative to an actuator, and at a distal end of each coil pipe relative to a proximal portion of a differing one of said plurality of articulatable segments; and
a plurality of tensioning members each housed in one of said plurality of coil pipes, wherein a proximal end of each of said plurality of tensioning members is coupled to said actuator, wherein a distal end of each of said plurality of tensioning members extends out the distal end of one of said plurality of coil pipes, and wherein the articulatable segments are actuated by the plurality of tensioning members, with the distal ends of at least two of the plurality of tensioning members being connected to differing articulatable segments of the plurality of articulatable segments to respectively actuate the differing articulatable segments in response to tensioning of the tensioning members,
wherein said plurality of coil pipes extend along each of the differing articulatable segments in a spiral pattern; and
wherein the articulatable segments comprise:
a proximal vertebra control ring located in a proximal portion of the articulatable segments, a distal vertebra control ring located in a distal portion of the articulatable segments, and at least one intermediate vertebra control ring disposed between the proximal and distal vertebra control rings,
wherein each of the proximal and distal vertebra control rings includes a plurality of bypass passages respectively arranged to receive and route the coil pipes in the spiral pattern, and
wherein the at least one intermediate vertebra control ring has a single, centrally disposed passage, the coil pipes passing through the centrally disposed passage as the coil pipes extend in the spiral pattern from the proximal vertebra control ring to the distal vertebra control ring.

2. The system according to claim 1, wherein each of the proximal and distal vertebra control rings comprises four bypass passages located at quadrants of the proximal and distal vertebra control rings.

3. The system according to claim 1, wherein said spiral pattern comprises an approximate integral number of approximately full spiral turns along each of the differing articulatable segments.

4. The system according to claim 3, wherein said approximate integral number is approximately one.

5. The system according to claim 1, wherein said plurality of coil pipes are constructed from approximately round wire.

6. The system according to claim 1, wherein said plurality of coil pipes are constructed from D-shaped wires.

7. The system according to claim 1, wherein said plurality of coil pipes are centerless ground.

8. The system according to claim 1, wherein each coil pipe comprises:
a wire coiled into a plurality of windings to form the coil pipe, wherein a cross-section of each of the plurality of windings comprises:

two approximately parallel approximately flat sides extending in a direction along a longitudinal axis of the pipe and between first and second oppositely disposed extremities of the cross-section, wherein the first extremity has a convex surface, and wherein the second extremity has a concave surface, wherein the concave and convex surfaces of adjacent windings of the plurality of windings approximately nest with one another; and wherein said approximately parallel flat sides of the plurality of windings together define an interior and an exterior of said pipe.

9. The system according to claim 8, wherein the wire is a solid wire.

10. The system according to claim 8, wherein said convex surface and said concave surface each have an approximately curved shape.

11. The system according to claim 10, wherein said approximately curved shape is a partial circumference of an approximate circle.

12. The system according to claim 8, wherein said convex surface and said concave surface have an approximately angular shape.

13. The system according to claim 12, wherein said angular shape is an approximate V-shape.

14. The system according to claim 1, wherein the coil pipes are made of solid wire.

15. The system according to claim 1, wherein each of the proximal and distal vertebra control rings comprises four bypass passages located at quadrants of the proximal and distal vertebra control rings; and wherein the quadrants are formed by a body and a cross bar within the body.

16. The system according to claim 15, wherein the cross bar pivots relative to the body of the proximal vertebrae control ring.

17. The system according to claim 1, wherein more than one tensioning member and more than one coil pipe extend through each of the bypass passages of the proximal and distal vertebra control rings.

18. The system according to claim 1, wherein the bypass passages of the proximal and distal vertebra control rings are rotationally offset relative to one another with respect to a longitudinal axis of the elongate body to route the plurality of coil pipes in the spiral pattern.

19. The system according to claim 1, wherein the centrally disposed passage of the at least one intermediate vertebra control ring is configured to provide a relatively unconstrained space in which the coil pipes are received.

20. A system for managing the transmission of force in an articulating device, the system comprising:

an elongate body comprising a plurality of articulatable segments;

a plurality of Bowden-type cables, wherein a proximal end of each of the Bowden-type cables is coupled to an actuator and distal ends of at least two of the Bowden-type cables are connected to differing articulatable segments of the plurality of articulatable segments to respectively actuate the differing articulatable segments in response to tensioning of the Bowden-type cables, wherein the at least two of the Bowden-type cables extend along each of the differing articulatable segments in a spiral pattern;

wherein the Bowden-type cables comprise coils wound into coil pipes and tensioning members that pass through the coil pipes, wherein the coil pipes have an approximately flat outer surface along an axial length of the coil pipe;

wherein the articulatable segments comprise:

a proximal vertebra control ring located in a proximal portion of the articulatable segments, a distal vertebra control ring located in a distal portion of the articulatable segments, and at least one intermediate vertebra control ring disposed between the proximal and distal vertebra control rings, wherein each of the proximal and distal vertebra control rings include a plurality of bypass passages, the bypass passages of the proximal and distal vertebra control rings being respectively arranged to receive and route the Bowden-type cables in the spiral pattern, and wherein the at least one intermediate vertebra control ring has a single, centrally disposed passage, the Bowden-type cables passing through the centrally disposed passage as the Bowden-type cables extend in the spiral pattern from the proximal vertebra control ring to the distal vertebra control ring.

21. The system according to claim 20, wherein said spiral pattern comprises an approximate integral number of approximately full spiral turns along each of said plurality of articulatable segments.

22. The system according to claim 21, wherein said approximate integral number is approximately one.

23. The system according to claim 20, wherein each of the proximal and distal vertebra control rings comprises four bypass passages located at quadrants of the proximal and distal vertebra control rings.

24. The system according to claim 20, wherein the bypass passages of the proximal and distal vertebra control rings are rotationally offset relative to one another with respect to a longitudinal axis of the elongate body to route the plurality of Bowden-type cables in the spiral pattern.

25. The system according to claim 20, wherein the centrally disposed passage of the at least one intermediate vertebra control ring is configured to provide a relatively unconstrained space in which the Bowden-type cables are received.

* * * * *